US008273854B2

(12) United States Patent
Glaesner et al.

(10) Patent No.: US 8,273,854 B2
(45) Date of Patent: Sep. 25, 2012

(54) GLP-1 ANALOG FUSION PROTEINS

(75) Inventors: Wolfgang Glaesner, Indianapolis, IN (US); Rohn Lee Millican, Jr., Indianapolis, IN (US); Andrew Mark Vick, Fishers, IN (US)

(73) Assignee: Eli Lilly and Company, Indianapolis, IN (US)

( * ) Notice: Subject to any disclaimer, the term of this patent is extended or adjusted under 35 U.S.C. 154(b) by 704 days.

(21) Appl. No.: 12/262,832

(22) Filed: Oct. 31, 2008

(65) Prior Publication Data
US 2009/0074769 A1 Mar. 19, 2009

Related U.S. Application Data

(62) Division of application No. 10/558,627, filed as application No. PCT/US2004/015595 on Jun. 10, 2004, now Pat. No. 7,452,966.

(60) Provisional application No. 60/477,880, filed on Jun. 12, 2003.

(51) Int. Cl.
*A61K 38/26* (2006.01)
*C07K 14/605* (2006.01)
(52) U.S. Cl. ............... 530/324; 514/11.7; 530/308
(58) Field of Classification Search .................. None
See application file for complete search history.

(56) References Cited

U.S. PATENT DOCUMENTS

| | | | |
|---|---|---|---|
| 5,624,821 | A | 4/1997 | Winter et al. |
| 5,627,267 | A | 5/1997 | Lyman et al. |
| 5,908,626 | A | 6/1999 | Chang |
| 6,190,909 | B1 | 2/2001 | Levinson |
| 6,191,102 | B1 | 2/2001 | DiMarchi |
| 6,376,653 | B1 | 4/2002 | Holmes et al. |
| 6,992,174 | B2 | 1/2006 | Gillies et al. |
| 7,141,547 | B2 | 11/2006 | Rosen et al. |
| 7,271,149 | B2 * | 9/2007 | Glaesner et al. ............... 514/12 |
| 7,452,966 | B2 * | 11/2008 | Glaesner et al. ............... 530/324 |
| 2003/0082749 | A1 | 5/2003 | Sun et al. |
| 2004/0175824 | A1 | 9/2004 | Sun et al. |

FOREIGN PATENT DOCUMENTS

| | | |
|---|---|---|
| WO | 9604388 | 12/1996 |
| WO | 9700319 | 1/1997 |
| WO | 9728267 | 8/1997 |
| WO | 0069911 | 11/2000 |
| WO | 0198331 | 12/2001 |
| WO | WO 02/46227 | 6/2002 |

OTHER PUBLICATIONS

Issacs, et al. "A Therapeutic Human IgG4 Monoclonal Antibody That Depletes Target Cells in Humans." Clin. Exp. Immunology, vol. 106, pp. 427-433, 1996.
Danlin Xu et al.; In Vitro Characterization of Five Humanized OKT3 Effector Function Variant Antibodies, Cellular Immunology, (2000), 200, pp. 16-26.
Manjula P. Reddy et al.; Elimination of Fc Receptor-Dependent Effector Functions of a Modified IgG4 Monoclonal Antibody to Human CD4, The Journal of Immunology, (2000), 164(4), pp. 1925-1933.
Jefferis et al; Interaction sites on human IgG-Fc for FcyR: current models, Immunology Letters 82 (2002) 57-65.
Burton, et al., "Human Antibody Effector Function," Adv Immunol, vol. 51, pp. 1-84 (1992).
Greenwood J, et al., "Structural Motifs Involved in Human IgG Antibody Effector Functions," Eur J Immunol, vol. 23(5), pp. 1098-1104 (1993).
Newman, et al., "Modification of the Fc Region of a Primatized IgG Antibody to Human CD4 Retains Its Ability to Modulate CD4 Receptors But Does Not Deplete CD4(+) T Cells in Chimpanzees," Clin Immunol, vol. 98(2), pp. 164-174 (2001).
Hutchins JT, et al., "Improved Biodistribution, Tumor Targeting, and Reduced Immunogenicity in Mice With A Gamma 4 Variant of Campath-1H," Proc Natl Acad Sci USA, vol. 92(26), pp. 11980-11984 (1995).
Isaacs JD, et al., "The Contribution of Fc Gamma Receptor Binding and The Influence of C(H)1 and C(H)3 Domains On In Vivo Effector Function," J Immunol, vol. 161(8), pp. 3862-3869 (1998).
Taylor L, et al., "In Vitro and In Vivo Activities of OX40 (CD134)-IgG Fusion Protein Isoforms With Different Levels of Immune-Effector Functions," J. Leukoc Biol, vol. 72(3), pp. 522-529 (2002).
Brekke OH, et al., "Tailoring Natural Effector Functions. Antibody Engineering Beyond Humanization," Methods Mol Biol, vol. 207, pp. 383-391 (2003).
Tao MH, et al., "Structural Features of Human Immunoglobulin G That Determine Isotype-Specific Differences In Complement Activation," J Exp Med, vol. 178(2), pp. 661-667 (1993).
Ghetie V, et al., Multiple Roles for the Major Histocompatibility Complex Class I-Related Receptor FcRn, Annu Rev Immunol, vol. 18, pp. 739-766 (2000).
West, et al., Crystal Structure and Immunoglobulin G Binding Properties of the Human Major Histocompatibility Complex-Related Fc Receptor(,), Biochemistry, vol. 39(32), pp. 9698-9708 (2000).
Gillies SD, et al., "Improving the Efficacy of Antibody-Interleukin 2 Fusion Proteins By Reducing Their Interaction with Fc Receptors," Cancer Res, vol. 59(9), pp. 2159-2166 (1999).
Wawrzynczak EJ, et al., "Recombinant Mouse Monoclonal Antibodies With Single Amino Acid Substitutions Affecting Clq and High Affinity Fc Receptor Binding Have Identical Serum Half-Lives in the BALB/c Mouse," Mol Immunol, vol. 29(2), pp. 221-227 (1992).
Canfield SM, et al., "The Binding Affinity of Human IgG for its High Affinity Fc Receptor is Determined by Multiple Amino Acids in the CH2 Domaina and is Modulated by the Hinge Region," J Exp Med., vol. 173(6), pp. 1483-1491 (1991).
Angal S. et al., A single Amino Acid Substitution Abolishes the Heterogeneity of Chimeric Mouse/Human (IgG4) Antibody, "Molecular Immunology," vol. 30, No. 1, pp. 105-108, (1993).

(Continued)

*Primary Examiner* — Cecilia J Tsang
*Assistant Examiner* — Ronald T Niebauer
(74) *Attorney, Agent, or Firm* — Ted J. Ebersole; Gregory A. Cox

(57) ABSTRACT

The invention provides specific GLP-1 analogs fused to specific IgG4-Fc derivatives. These fusion proteins have an increased half-life, decreased immunogenicity, and reduce effector activity. The fusion proteins are useful in treating diabetes, obesity, irritable bowel syndrome and other conditions that would be benefited by lowering plasma glucose, inhibiting gastric and/or intestinal motility and inhibiting gastric and/or intestinal emptying, or inhibiting food intake.

6 Claims, No Drawings

OTHER PUBLICATIONS

Request for Ex Parte Reexamination of U.S. Patent No. 7,452,966 filed Jun. 30, 2011.
Order Granting Request for Ex Parte Reexamination mailed Jul. 27, 2011.
Notice of Intent to Issue Ex Parte Reexamination Certificate mailed Dec. 13, 2011.
Ex Parte Reexamination Certificate issued Jan. 31, 2012.
Knudsen et al., Potent Derivatives of glucagon-like Peptide-1 with Pharmacokinetic Properties Suitable for Once Daily Admin., J.Med. Chem. 43(9): 1664-1669, (2000).
STN Registry Entry, 923950-08-7, Mar. 1, 2007, 2 pages.

* cited by examiner

SEQUENCE LISTING

<160> NUMBER OF SEQ ID NOS: 21

<210> SEQ ID NO 1
<211> LENGTH: 31
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Gly or Val

<400> SEQUENCE: 1

His Xaa Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly
            20                  25                  30

<210> SEQ ID NO 2
<211> LENGTH: 31
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Gly or Val

<400> SEQUENCE: 2

His Xaa Glu Gly Thr Phe Thr Ser Asp Val Ser Ser Tyr Leu Glu Glu
1               5                   10                  15

Gln Ala Ala Lys Glu Phe Ile Ala Trp Leu Lys Asn Gly Gly Gly
            20                  25                  30

<210> SEQ ID NO 3
<211> LENGTH: 31
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Gly or Val

<400> SEQUENCE: 3

His Xaa Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Pro
            20                  25                  30

<210> SEQ ID NO 4
<211> LENGTH: 31
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Gly or Val

<400> SEQUENCE: 4

His Xaa Glu Gly Thr Phe Thr Ser Asp Val Ser Ser Tyr Leu Glu Glu
1               5                   10                  15

Gln Ala Ala Lys Glu Phe Ile Ala Trp Leu Lys Asn Gly Gly Pro
            20                  25                  30

<210> SEQ ID NO 5
<211> LENGTH: 30
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Gly or Val

<400> SEQUENCE: 5

His Xaa Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly
            20                  25                  30

<210> SEQ ID NO 6
<211> LENGTH: 30
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Gly or Val

<400> SEQUENCE: 6

His Xaa Glu Gly Thr Phe Thr Ser Asp Val Ser Ser Tyr Leu Glu Glu
1               5                   10                  15

Gln Ala Ala Lys Glu Phe Ile Ala Trp Leu Lys Asn Gly Gly
            20                  25                  30

<210> SEQ ID NO 7
<211> LENGTH: 230
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (16)..(16)
<223> OTHER INFORMATION: Xaa at position 16 is Pro or Glu
<220> FEATURE:
<221> NAME/KEY: MISC_FEATURE
<222> LOCATION: (17)..(17)
<223> OTHER INFORMATION: Xaa at position 17 is Phe, Val, or Ala
<220> FEATURE:
<221> NAME/KEY: MISC_FEATURE
<222> LOCATION: (18)..(18)
<223> OTHER INFORMATION: Xaa at position 18 is Leu, Glu, or Ala
<220> FEATURE:
<221> NAME/KEY: MISC_FEATURE
<222> LOCATION: (80)..(80)
<223> OTHER INFORMATION: Xaa at position 80 is Asn or Ala
<220> FEATURE:
<221> NAME/KEY: MISC_FEATURE
<222> LOCATION: (230)..(230)
<223> OTHER INFORMATION: Xaa at position 230 is Lys or is absent

<400> SEQUENCE: 7

Ala Glu Ser Lys Tyr Gly Pro Pro Cys Pro Pro Cys Pro Ala Pro Xaa
1               5                   10                  15

Xaa Xaa Gly Gly Pro Ser Val Phe Leu Phe Pro Pro Lys Pro Lys Asp
            20                  25                  30

Thr Leu Met Ile Ser Arg Thr Pro Glu Val Thr Cys Val Val Val Asp
        35                  40                  45

Val Ser Gln Glu Asp Pro Glu Val Gln Phe Asn Trp Tyr Val Asp Gly
    50                  55                  60

Val Glu Val His Asn Ala Lys Thr Lys Pro Arg Glu Glu Gln Phe Xaa
65                  70                  75                  80

Ser Thr Tyr Arg Val Val Ser Val Leu Thr Val Leu His Gln Asp Trp
                85                  90                  95

Leu Asn Gly Lys Glu Tyr Lys Cys Lys Val Ser Asn Lys Gly Leu Pro
            100                 105                 110

Ser Ser Ile Glu Lys Thr Ile Ser Lys Ala Lys Gly Gln Pro Arg Glu
        115                 120                 125

Pro Gln Val Tyr Thr Leu Pro Pro Ser Gln Glu Glu Met Thr Lys Asn
    130                 135                 140

-continued

```
Gln Val Ser Leu Thr Cys Leu Val Lys Gly Phe Tyr Pro Ser Asp Ile
145                 150                 155                 160

Ala Val Glu Trp Glu Ser Asn Gly Gln Pro Glu Asn Asn Tyr Lys Thr
            165                 170                 175

Thr Pro Pro Val Leu Asp Ser Asp Gly Ser Phe Phe Leu Tyr Ser Arg
                180                 185                 190

Leu Thr Val Asp Lys Ser Arg Trp Gln Glu Gly Asn Val Phe Ser Cys
            195                 200                 205

Ser Val Met His Glu Ala Leu His Asn His Tyr Thr Gln Lys Ser Leu
        210                 215                 220

Ser Leu Ser Leu Gly Xaa
225                 230

<210> SEQ ID NO 8
<211> LENGTH: 15
<212> TYPE: PRT
<213> ORGANISM: Artificial
<220> FEATURE:
<223> OTHER INFORMATION: Synthetic Construct

<400> SEQUENCE: 8

Gly Gly Gly Gly Ser Gly Gly Gly Gly Ser Gly Gly Gly Gly Ser
1               5                   10                  15

<210> SEQ ID NO 9
<211> LENGTH: 31
<212> TYPE: PRT
<213> ORGANISM: Homo sapiens

<400> SEQUENCE: 9

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 10
<211> LENGTH: 71
<212> TYPE: PRT
<213> ORGANISM: Artificial
<220> FEATURE:
<223> OTHER INFORMATION: Synthetic Construct

<400> SEQUENCE: 10

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Arg Gly Gly
            20                  25                  30

Gly Gly Ser Gly Gly Gly Gly Ser Gly Gly Gly Gly Ser Gly Gly
        35                  40                  45

Gly Gly Ser Gly Gly Gly Gly Ser Gly Gly Gly Gly Ser Ala Glu Ser
    50                  55                  60

Lys Tyr Gly Pro Pro Cys Pro
65                  70

<210> SEQ ID NO 11
<211> LENGTH: 9
<212> TYPE: PRT
<213> ORGANISM: Artificial
<220> FEATURE:
<223> OTHER INFORMATION: Synthetic Construct

<400> SEQUENCE: 11
```

Trp Leu Val Lys Gly Arg Gly Gly Gly
1               5

<210> SEQ ID NO 12
<211> LENGTH: 7
<212> TYPE: PRT
<213> ORGANISM: Artificial
<220> FEATURE:
<223> OTHER INFORMATION: Synthetic Construct

<400> SEQUENCE: 12

Trp Leu Val Lys Gly Gly Gly
1               5

<210> SEQ ID NO 13
<211> LENGTH: 7
<212> TYPE: PRT
<213> ORGANISM: Artificial
<220> FEATURE:
<223> OTHER INFORMATION: Synthetic Construct

<400> SEQUENCE: 13

Trp Leu Lys Asn Gly Gly Gly
1               5

<210> SEQ ID NO 14
<211> LENGTH: 7
<212> TYPE: PRT
<213> ORGANISM: Artificial
<220> FEATURE:
<223> OTHER INFORMATION: Synthetic Construct

<400> SEQUENCE: 14

Trp Leu Val Lys Gly Gly Pro
1               5

<210> SEQ ID NO 15
<211> LENGTH: 7
<212> TYPE: PRT
<213> ORGANISM: Artificial
<220> FEATURE:
<223> OTHER INFORMATION: Synthetic Construct

<400> SEQUENCE: 15

Trp Leu Lys Asn Gly Gly Pro
1               5

<210> SEQ ID NO 16
<211> LENGTH: 6
<212> TYPE: PRT
<213> ORGANISM: Artificial
<220> FEATURE:
<223> OTHER INFORMATION: Synthetic Construct

<400> SEQUENCE: 16

Trp Leu Val Lys Gly Gly
1               5

<210> SEQ ID NO 17
<211> LENGTH: 6
<212> TYPE: PRT
<213> ORGANISM: Artificial
<220> FEATURE:
<223> OTHER INFORMATION: Synthetic Construct

<400> SEQUENCE: 17

Trp Leu Lys Asn Gly Gly

<210> SEQ ID NO 18
<211> LENGTH: 6
<212> TYPE: PRT
<213> ORGANISM: Homo sapiens

<400> SEQUENCE: 18

Pro Pro Cys Pro Ser Cys
1               5

<210> SEQ ID NO 19
<211> LENGTH: 22
<212> TYPE: PRT
<213> ORGANISM: Artificial
<220> FEATURE:
<223> OTHER INFORMATION: Synthetic Construct

<400> SEQUENCE: 19

Gly Ser Gly Gly Gly Gly Ser Gly Gly Gly Gly Ser Gly Gly Gly Gly
1               5                   10                  15

Ser Gly Gly Gly Gly Ser
            20

<210> SEQ ID NO 20
<211> LENGTH: 825
<212> TYPE: DNA
<213> ORGANISM: Homo sapiens

<400> SEQUENCE: 20
cacggcgagg gcaccttcac ctccgacgtg tcctcctatc tcgaggagca ggccgccaag      60
gaattcatcg cctggctggt gaagggcggc ggcggtggtg gtggctccgg aggcggcggc     120
tctggtggcg gtggcagcgc tgagtccaaa tatggtcccc catgcccacc ctgcccagca     180
cctgaggccg ccggggggacc atcagtcttc ctgttccccc caaaacccaa ggacactctc     240
atgatctccc ggacccctga ggtcacgtgc gtggtggtgg acgtgagcca ggaagacccc     300
gaggtccagt tcaactggta cgtggatggc gtggaggtgc ataatgccaa gacaaagccg     360
cgggaggagc agttcaacag cacgtaccgt gtggtcagcg tcctcaccgt cctgcaccag     420
gactggctga acggcaagga gtacaagtgc aaggtctcca acaaaggcct cccgtcctcc     480
atcgagaaaa ccatctccaa agccaaaggg cagccccgag agccacaggt gtacaccctg     540
cccccatccc aggaggagat gaccaagaac caggtcagcc tgacctgcct ggtcaaaggc     600
ttctacccca gcgacatcgc cgtggagtgg gaaagcaatg ggcagccgga gaacaactac     660
aagaccacgc ctcccgtgct ggactccgac ggctccttct tcctctacag caggctaacc     720
gtggacaaga gcaggtggca ggaggggaat gtcttctcat gctccgtgat gcatgaggct     780
ctgcacaacc actacacaca gaagagcctc tccctgtctc tgggt                    825

<210> SEQ ID NO 21
<211> LENGTH: 30
<212> TYPE: PRT
<213> ORGANISM: Artificial
<220> FEATURE:
<223> OTHER INFORMATION: Synthetic Construct

<400> SEQUENCE: 21

Gly Gly Gly Gly Ser Gly Gly Gly Gly Ser Gly Gly Gly Gly Ser Gly
1               5                   10                  15

```
Gly Gly Gly Ser Gly Gly Gly Gly Ser Gly Gly Gly Ser
            20              25              30
```

GLP-1 ANALOG FUSION PROTEINS

This application is a divisional of U.S. Ser. No. 10/558,627 (U.S. Pat. No. 7,452,966) filed Nov. 29, 2005 which is the national phase application, under 35 U.S.C. 371, for PCT/US04/15595 filed Jun. 10, 2004 which claims the priority of U.S. provisional application No. 60/477,880, filed Jun. 12, 2003.

FIELD OF THE INVENTION

The present invention relates to glucagon-like peptide analogs fused to proteins that have the effect of extending the in vivo half-life of the peptides. These fusion proteins can be used to treat diabetes as well as a variety of other conditions or disorders.

Glucagon-like peptide-1 (GLP-1) analogs and derivatives show promise in clinical trials for the treatment of type 2 diabetes. GLP-1 induces numerous biological effects such as stimulating insulin secretion, inhibiting glucagon secretion, inhibiting gastric emptying, inhibiting gastric motility or intestinal motility, and inducing weight loss. A significant characteristic of GLP-1 is its ability to stimulate insulin secretion without the associated risk of hypoglycemia that is seen when using insulin therapy or some types of oral therapies that act by increasing insulin expression.

The usefulness of therapy involving GLP-1 peptides has been limited by the fact that GLP-1(1-37) is poorly active, and the two naturally occurring truncated peptides, GLP-1(7-37)OH and GLP-1(7-36)NH$_2$, are rapidly cleared in vivo and have extremely short in vivo half lives. It is known that endogenously produced dipeptidyl-peptidase IV (DPP-IV) inactivates circulating GLP-1 peptides by removing the N-terminal histidine and alanine residues and is a major reason for the short in vivo half-life.

Various approaches have been undertaken to extend the elimination half-life of a GLP-1 peptide or reduce clearance of the peptide from the body while maintaining biological activity. One approach involves fusing a GLP-1 peptide to the Fc portion of an immunoglobulin. Immunoglobulins typically have long circulating half-lives in vivo. For example, IgG molecules can have a half-life in humans of up to 23 days. The Fc portion of the immunoglobulin is responsible, in part, for this in vivo stability. GLP-1-Fc fusion proteins take advantage of the stability provided by the Fc portion of an immunoglobulin while preserving the biological activity of the GLP-1 molecule.

Although this approach is feasible for GLP-1 therapeutics (See WO 02/46227), there is a general concern regarding the antigenicity of various fusion proteins when administered repeatedly over prolonged periods of time. This is especially a concern for GLP-1-Fc fusion therapeutics as a patient with diabetes must be treated for her entire life once diagnosed with the disease. In addition, Fc fusion protein therapeutics can be a concern if the Fc portion retains unwanted effector functions.

The present invention seeks to overcome the problems associated with the potential immunogenicity and effector activity associated with administration of GLP-1-Fc fusions by identifying specific GLP-1-Fc fusion proteins that have a reduced risk of inducing an immune response after repeated and prolonged administration and no longer have effector function. These specific fusion proteins have substitutions at various positions in the GLP-1 portion as well as the Fc portion of the molecule. The substitutions described herein provide increased potency, increased in vivo stability, elimination of effector function and decreased likelihood the molecule will be recognized by the adaptive elements of the immune system.

Compounds of the present invention include heterologous fusion proteins comprising a GLP-1 analog comprising a sequence selected from the group consisting of a)
(SEQ ID NO:1)
His-Xaa$_8$-Glu-Gly-Thr-Phe-Thr-Ser-Asp-Val-Ser-Ser-
Tyr-Leu-Glu-Glu-Gln-Ala-Ala-Lys-Glu-Phe-Ile-Ala-
Trp-Leu-Val-Lys-Gly-Gly-Gly wherein Xaa$_8$ is selected from Gly and Val;

b)
(SEQ ID NO:2)
His-Xaa$_8$-Glu-Gly-Thr-Phe-Thr-Ser-Asp-Val-Ser-Ser-
Tyr-Leu-Glu-Glu-Gln-Ala-Ala-Lys-Glu-Phe-Ile-Ala-
Trp-Leu-Lys-Asn-Gly-Gly-Gly wherein Xaa$_8$ is selected from Gly and Val;

c)
(SEQ ID NO:3)
His-Xaa$_8$-Glu-Gly-Thr-Phe-Thr-Ser-Asp-Val-Ser-Ser-
Tyr-Leu-Glu-Glu-Gln-Ala-Ala-Lys-Glu-Phe-Ile-Ala-
Trp-Leu-Val-Lys-Gly-Gly-Pro wherein Xaa$_8$ is selected from Gly and Val;

d)
(SEQ ID NO:4)
His-Xaa$_8$-Glu-Gly-Thr-Phe-Thr-Ser-Asp-Val-Ser-Ser-
Tyr-Leu-Glu-Glu-Gln-Ala-Ala-Lys-Glu-Phe-Ile-Ala-
Trp-Leu-Lys-Asn-Gly-Gly-Pro wherein Xaa$_8$ is selected from Gly and Val;

e)
(SEQ ID NO:5)
His-Xaa$_8$-Glu-Gly-Thr-Phe-Thr-Ser-Asp-Val-Ser-Ser-
Tyr-Leu-Glu-Glu-Gln-Ala-Ala-Lys-Glu-Phe-Ile-Ala-
Trp-Leu-Val-Lys-Gly-Gly wherein Xaa$_8$ is selected from Gly and Val;

f)
(SEQ ID NO:6)
His-Xaa$_8$-Glu-Gly-Thr-Phe-Thr-Ser-Asp-Val-Ssr-Ser-
Tyr-Leu-Glu-Glu-Gln-Ala-Ala-Lys-Glu-Phe-Ile-Ala-
Trp-Leu-Lys-Asn-Gly-Gly wherein Xaa$_8$ is selected from Gly and Val;
fused to the Fc portion of an immunoglobulin comprising the sequence of SEQ ID NO:7

(SEQ ID NO:7)
Ala-Glu-Ser-Lys-Tyr-Gly-Pro-Pro-Cys-Pro-Pro-Cys-Pro-Ala-Pro-Xaa₁₆-Xaa₁₇-Xaa₁₈-Gly-Gly-Pro-Ser-Val-Phe-Leu-Phe-Pro-Pro-Lys-Pro-Lys-Asp-Thr-Leu-Met-Ile-Ser-Arg-Thr-Pro-Glu-Val-Thr-Cys-Val-Val-Val-Asp-Val-Ser-Gln-Glu-Asp-Pro-Glu-Val-Gln-Phe-Asn-Trp-Tyr-Val-Asp-Gly-Val-Glu-Val-His-Asn-Ala-Lys-Thr-Lys-Pro-Arg-Glu-Glu-Gln-Phe-Xaa₈₀-Ser-Thr-Tyr-Arg-Val-Val-Ser-Val-Leu-Thr-Val-Leu-His-Gln-Asp-Trp-Leu-Asn-Gly-Lys-Glu-Tyr-Lys-Cys-Lys-Val-Ser-Asn-Lys-Gly-Leu-Pro-Ser-Ser-Ile-Glu-Lys-Thr-Ile-Ser-Lys-Ala-Lys-Gly-Gln-Pro-Arg-Glu-Pro-Gln-Val-Tyr-Thr-Leu-Pro-Pro-Ser-Gln-Glu-Glu-Met-Thr-Lys-Asn-Gln-Val-Ser-Leu-Thr-Cys-Leu-Val-Lys-Gly-Phe-Tyr-Pro-Ser-Asp-Ile-Ala-Val-Glu-Trp-Glu-Ser-Asn-Gly-Gln-Pro-Glu-Asn-Asn-Tyr-Lys-Thr-Thr-Pro-Pro-Val-Leu-Asp-Ser-Asp-Gly-Ser-Phe-Phe-Leu-Tyr-Ser-Arg-Leu-Thr-Val-Asp-Lys-Ser-Arg-Trp-Gln-Glu-Gly-Asn-Val-Phe-Ser-Cys-Ser-Val-Met-His-Glu-Ala-Leu-His-Asn-His-Tyr-Thr-Gln-Lys-Ser-Leu-Ser-Leu-Ser-Leu-Gly-Xaa₂₃₀ wherein:
Xaa at position 16 is Pro or Glu;
Xaa at position 17 is Phe, Val, or Ala;
Xaa at position 18 is Leu, Glu, or Ala;
Xaa at position 80 is Asn or Ala; and
Xaa at position 230 is Lys or is absent.

The C-terminus of the GLP-1 analog portion and the N-terminus of the Fc portion of the heterologous fusion proteins of the present invention are preferably fused together via 1, 1.5 or 2 repeats of a G-rich peptide linker having the sequence Gly-Gly-Gly-Gly-Ser-Gly-Gly-Gly-Gly-Ser-Gly-Gly-Gly-Gly-Ser (SEQ ID NO:8).

The present invention also includes polynucleotides encoding the heterologous fusion proteins of the present invention, as well as vectors and host cells comprising such polynucleotides. Methods of treating patients suffering from non-insulin dependent as well as insulin dependent diabetes mellitus, obesity, and various other disorders and conditions comprising administering the heterologous fusion proteins discussed herein are also encompassed by the present invention.

The heterologous fusion proteins of the present invention comprise a GLP-1 analog portion and an Fc portion. The GLP-1 analog portion and the Fc portion comprise substitutions to the native GLP-1 sequence and the human IgG4 sequence respectively that provide the protein with increased potency and in vivo stability compared to native GLP-1 or GLP-1 analogs not fused to an Fc sequence while decreasing the potential for inducing antibody formation after prolonged and repeated administration in humans.

Native GLP-1 is processed in vivo such that the first 6 amino acids are cleaved from the molecule. Thus, by custom in the art, the amino terminus of GLP-1 has been assigned the number 7 and the carboxy-terminus, number 37. The other amino acids in the polypeptide are numbered consecutively as shown in SEQ ID NO:9. For example, position 8 is alanine and position 22 is glycine. The processed peptide may be further modified in vivo such that the C-terminal glycine residue is removed and replaced with an amide group. Thus, GLP-1(7-37)OH and GLP-1(7-36)amide represent the two native forms of the molecule. GLP-1(7-37)OH has the amino acid sequence of SEQ ID NO:9:

(SEQ ID NO:9)
⁷His-Ala-Glu-¹⁰Gly-Thr-Phe-Thr-Ser-¹⁵Asp-Val-Ser-Ser-Tyr-²⁰Leu-Glu-Gly-Gln-Ala-²⁵Ala-Lys-Glu-Phe-Ile-³⁰Ala-Trp-Leu-Val-Lys-³⁵Gly-Arg-³⁷Gly

The GLP-1 analog portion of the heterologous fusion protein comprises three primary substitutions at positions 8, 22, and 36 relative to native GLP-1(7-37). The substitution at position 8 reduces the rate at which the endogenous enzyme dipeptidyl-peptidase IV (DPP-IV) inactivates the analog. DPP-IV cleaves native GLP-1 between the $2^{nd}$ and $3^{rd}$ amino acids (between position 8 and 9) and the resulting molecule is less active. Thus, the heterologous fusion proteins of the present invention are DPP-IV resistant. The substitution at position 22 reduces the potential of the molecule to aggregate and increases the potency of the molecule. The substitution at position 36 in the context of the analog with changes at 8 and 22 as well as in the context of the entire fusion protein reduces the risk that the fusion protein will induce a neutralizing immune response after repeated and prolonged administration in humans.

The central event in the generation of both humoral and cell-mediated immune responses is the activation and clonal expansion of T-helper ($T_H$) cells. TH cell activation is initiated by interaction of the T-cell receptor (TCR)-CD3 complex with a processed antigenic peptide bound to a class II major histocompatibility (MHC) molecule in the presence of an antigen-presenting cell (APC). Interaction of a $T_H$ cell with antigen initiates a cascade of biochemical events that induces the resting $T_H$ cell to enter the cell cycle ($G_0$ to $G_1$ transition). The activated T cell progresses through the cell cycle, proliferating and differentiating into memory cells or effector cells.

The following sequence was analyzed to identify potential epitopes:

(SEQ ID NO:10)
His-Gly-Glu-Gly-Thr-Phe-Thr-Ser-Asp-Val-Ser-Ser-Tyr-Leu-Glu-Glu-Gln-Ala-Ala-Lys-Glu-Phe-Ile-Ala-Trp-Leu-Val-Lys-Gly-Arg-Gly-Gly-Gly-Gly-Ser-Gly-Gly-Gly-Gly-Ser-Gly-Gly-Gly-Gly-Ser-Gly-Gly-Gly-Gly-Ser-Gly-Gly-Gly-Gly-Ser-Gly-Gly-Gly-Gly-Ser-Ala-Glu-Ser-Lys-Tyr-Gly-Pro-Pro-Cys-Pro

This sequence is a GLP-1 analog sequence with changes at positions 8 and 22 relative to the native sequence followed by 2 copies of a G-rich linker sequence followed by the first 10 amino acids of an Fc region derived from human IgG4. Epitope as used herein refers to a region of a protein molecule to which an antibody can bind. An immunogenic epitope is defined as the part of the protein that elicits an antibody response when the whole protein is the immunogen. Epitope mapping involved the scanning of sequences using a sliding nine amino acid window coupled with advanced statistical analysis techniques to extract the information contained in these patterns. A proprietary software package known as Epi-Matrix™ was used to analyze the sequence and identify peptides that are highly likely to provoke an immune response when presented to T-cells. Eight highly common alleles were used in the analysis for Class II MHC receptor interaction. These alleles included DRB1*0101, DRB1*0301, DRB1*0401, DRB1*0701, DRB1*0801, DRB1*1101, DRB1*1301, and DRB1*1501.

A strong epitope was predicted to be located at the junction of the C-terminus of the GLP-1 analog portion and the beginning of the linker. The sequence of this epitope is Trp-Leu-Val-Lys-Gly-Arg-Gly-Gly-Gly (SEQ ID NO:11) which interacts with DRB1*0801. The present invention encompasses the discovery that this epitope can be eliminated by changing the GLP-1 analog C-terminus to one of the following sequences: Trp-Leu-Val-Lys-Gly-Gly-Gly (SEQ ID NO: 12); Trp-Leu-Lys-Asn-Gly-Gly-Gly (SEQ ID NO: 13); Trp-Leu-Val-Lys-Gly-Gly-Pro (SEQ ID NO: 14); Trp-Leu-Lys-Asn-Gly-Gly-Pro (SEQ ID NO:15); Trp-Leu-Val-Lys-Gly-Gly (SEQ ID NO: 16); and Trp-Leu-Lys-Asn-Gly-Gly (SEQ ID NO: 17).

The heterologous fusion proteins of the present invention contain an Fc portion which is derived from human IgG4, but comprises one or more substitutions compared to the wild-type human sequence. As used herein, the Fc portion of an immunoglobulin has the meaning commonly given to the term in the field of immunology. Specifically, this term refers to an antibody fragment which does not contain the two antigen binding regions (the Fab fragments) from the antibody. The Fc portion consists of the constant region of an antibody from both heavy chains, which associate through non-covalent interactions and disulfide bonds. The Fc portion can include the hinge regions and extend through the CH2 and CH3 domains to the c-terminus of the antibody. The Fc portion can further include one or more glycosylation sites.

There are five types of human immunoglobulins with different effector functions and pharmcokinetic properties. IgG is the most stable of the five types having a serum half-life in humans of about 23 days. There are four IgG subclasses (G1, G2, G3, and G4) each of which have different biological functions known as effector functions. These effector functions are generally mediated through interaction with the Fc receptor (FcγR) or by binding C1q and fixing complement. Binding to FcγR can lead to antibody dependent cell mediated cytolysis, whereas binding to complement factors can lead to complement mediated cell lysis. In designing heterologous Fc fusion proteins wherein the Fc portion is being utilized solely for its ability to extend half-life, it is important to minimize any effector function. Thus, the heterologous fusion proteins of the present invention are derived from the human IgG4 Fc region because of its reduced ability to bind FcγR and complement factors compared to other IgG subtypes. IgG4, however, has been shown to deplete target cells in humans [Issacs et al., (1996) Clin. Exp. Immunol. 106:427-433]. Because the heterologous fusion proteins of the present invention target beta cells in the pancreas to induce insulin expression, using an IgG4 derived region in an Fc fusion protein could initiate an immune response against the pancreatic beta cell through interaction of the fusion protein with the GLP-1 receptor present on pancreatic beta cells. Thus, the IgG4 Fc region which is part of the heterologous fusion proteins of the present invention contains substitutions that eliminate effector function. The IgG4 Fc portion of the fusion proteins of the present invention may contain one or more of the following substitutions: substitution of proline for glutamate at residue 233, alanine or valine for phenylalanine at residue 234 and alanine or glutamate for leucine at residue 235 (EU numbering, Kabat, E. A. et al. (1991) *Sequences of Proteins of Immunological Interest, 5th* Ed. U.S. Dept. of Health and Human Services, Bethesda, Md., NIH Publication no. 91-3242). These residues corresponds to positions 16, 17 and 18 in SEQ ID NO:7. Further, removing the N-linked glycosylation site in the IgG4 Fc region by substituting Ala for Asn at residue 297 (EU numbering) which corresponds to position 80 of SEQ ID NO:7 is another way to ensure that residual effector activity is eliminated in the context of a heterologous fusion protein.

In addition, the IgG4 Fc portion of the heterologous fusion proteins of the present invention contain a substitution that stabilizes heavy chain dimer formation and prevents the formation of half-IgG4 Fc chains. The heterologous fusion proteins of the present invention preferably exist as dimers joined together by disulfide bonds and various non-covalent interactions. Wild-type IgG4 contains a Pro-Pro-Cys-Pro-Ser-Cys (SEQ ID NO:18) motif beginning at residue 224 (EU numbering). This motif in a single GLP-1 analog-Fc chain forms disulfide bonds with the corresponding motif in another GLP-1 analog-Fc chain. However, the presence of serine in the motif causes the formation of single chain fusion proteins. The present invention encompasses heterologous Fc fusion proteins wherein the IgG4 sequence is further modified such that serine at position at 228 (EU numbering) is substituted with proline (amino acid residue 11 in SEQ ID NO:7).

The C-terminal lysine residue present in the native molecule may be deleted in the IgG4 derivative Fc portion of the heterologous fusion proteins discussed herein (position 230 of SEQ ID NO:7; deleted lysine referred to as des-K). Fusion proteins expressed in some cell types (such as NSO cells) wherein lysine is encoded by the C-terminal codon are heterogeneous in that a portion of the molecules have lysine as the C-terminal amino acid and a portion have lysine deleted. The deletion is due to protease action during expression in some types of mammalian cells. Thus, to avoid this heterogeneity, it is preferred that Fc fusion expression constructs lack a C-terminal codon for lysine.

It is preferred that the C-terminal amino acid of the GLP-1 analog portion discussed herein is fused to the N-terminus of the IgG4 Fc analog portion via a glycine-rich linker. The in vivo function and stability of the heterologous fusion proteins of the present invention can be optimized by adding small peptide linkers to prevent potentially unwanted domain interactions. Further, a glycine-rich linker provides some structural flexibility such that the GLP-1 analog portion can interact productively with the GLP-1 receptor on target cells such as the beta cells of the pancreas. These linkers, however, can significantly increase the risk that the fusion protein will be immunogenic in vivo. Thus, it is preferred that the length be no longer than necessary to prevent unwanted domain interactions and/or optimize biological activity and/or stability. The preferred glycine-rich linker comprises the sequence: Gly-Gly-Gly-Gly-Ser-Gly-Gly-Gly-Gly-Ser-Gly-Gly-Gly-Gly-Ser (SEQ ID NO:8). Although more copies of this linker may be used in the heterologous fusion proteins of the present invention, it is preferred that a single copy of this linker be used to minimize the risk of immunogenicity associated with prolonged and repeated administration.

Preferred GLP-1-Fc heterologous fusion proteins of the present invention include the following proteins: $Gly^8$-$Glu^{22}$-$Gly^{36}$-GLP-1(7-37)-1L-IgG4 (S228P), $Gly^8$-$Glu^{22}$-$Gly^{36}$-GLP-1(7-37)-1L-IgG4 (S228P, F234A, L235A), $Gly^8$-$Glu^{22}$-$Gly^{36}$-GLP-1(7-37)-1L-IgG4 (S228P, N297A), $Gly^8$-$Glu^{22}$-$Gly^{36}$-GLP-1(7-37)-1L-IgG4 (S228P, F234A, L235A, N297A), Gly$^8$-Glu$^{22}$-Gly$^{36}$-GLP-1(7-37)-1.5L-IgG4 (S228P), Gly$^8$-Glu$^{22}$-Gly$^{36}$-GLP-1(7-37)-1.5L-IgG4 (S228P, F234A, L235A), Gly$^8$-Glu$^{22}$-Gly$^{36}$-GLP-1(7-37)-1.5L-IgG4 (S228P, N297A), Gly$^8$-Glu$^{22}$-Gly$^{36}$-GLP-1(7-37)-1.5L-IgG4 (S228P, F234A, L235A, N297A), Gly$^8$-Glu$^{22}$-Gly$^{36}$-GLP-1(7-37)-2L-IgG4 (S228P), Gly$^8$-Glu$^{22}$-Gly$^{36}$-GLP-1(7-37)-2L-IgG4 (S228P, F234A, L235A), Gly$^8$-Glu$^{22}$-Gly$^{36}$-GLP-1(7-37)-2L-IgG4 (S228P, N297A), and Gly$^8$-Glu$^{22}$-Gly$^{36}$-GLP-1(7-37)-2L-IgG4 (S228P, F234A, L235A, N297A), and the Val$^8$ and des-K forms of all of the above.

The nomenclature used herein to refer to specific heterologous fusion proteins is defined as follows: Specific substitutions to the GLP-1 portion of the fusion protein are indicated using the specific amino acid being substituted followed by the residue number. GLP-1(7-37) indicates that the GLP-1 portion of the mature fusion protein begins with His at position 7 and ends with Gly at position 37. L refers to a linker with the sequence Gly-Gly-Gly-Gly-Ser-Gly-Gly-Gly-Gly-Ser-Gly-Gly-Gly-Gly-Ser (SEQ ID NO:8). The number immediately preceding the L refers to the number of linkers separating the GLP-1 portion from the Fc portion. A linker specified as 1.5L refers to the sequence Gly-Ser-Gly-Gly-Gly-Gly-Ser-Gly-Gly-Gly-Gly-Ser-Gly-Gly-Gly-Gly-Ser-Gly-Gly-Gly-Gly-Ser (SEQ ID NO:19) IgG4 refers to an analog of the human IgG4 Fc sequence specified as SEQ ID NO:7. Substitutions in the IgG4 Fc portion of the heterologous fusion protein are indicated in parenthesis. The wild-type amino acid is specified by its common abbreviation followed by the position number in the context of the entire IgG4 sequence using the EU numbering system followed by the amino acid being substituted at that position specified by its common abbreviation.

Although the heterologous fusion proteins of the present invention can be made by a variety of different methods, because of the size of the fusion protein, recombinant methods are preferred. For purposes of the present invention, as disclosed and claimed herein, the following general molecular biology terms and abbreviations are defined below.

"Base pair" or "bp" as used herein refers to DNA or RNA. The abbreviations A, C, G, and T correspond to the 5'-monophosphate forms of the deoxyribonucleosides (deoxy)adenosine, (deoxy)cytidine, (deoxy)guanosine, and thymidine, respectively, when they occur in DNA molecules. The abbreviations U, C, G, and A correspond to the 5'-monophosphate forms of the ribonucleosides uridine, cytidine, guanosine, and adenosine, respectively when they occur in RNA molecules. In double stranded DNA, base pair may refer to a partnership of A with T or C with G. In a DNA/RNA, heteroduplex base pair may refer to a partnership of A with U or C with G. (See the definition of "complementary", infra.)

"Digestion" or "Restriction" of DNA refers to the catalytic cleavage of the DNA with a restriction enzyme that acts only at certain sequences in the DNA ("sequence-specific endonucleases"). The various restriction enzymes used herein are commercially available and their reaction conditions, cofactors, and other requirements were used as would be known to one of ordinary skill in the art. Appropriate buffers and substrate amounts for particular restriction enzymes are specified by the manufacturer or can be readily found in the literature.

"Ligation" refers to the process of forming phosphodiester bonds between two double stranded nucleic acid fragments. Unless otherwise provided, ligation may be accomplished using known buffers and conditions with a DNA ligase, such as T4 DNA ligase.

"Plasmid" refers to an extrachromosomal (usually) self-replicating genetic element.

"Recombinant DNA cloning vector" as used herein refers to any autonomously replicating agent, including, but not limited to, plasmids and phages, comprising a DNA molecule to which one or more additional DNA segments can or have been added.

"Recombinant DNA expression vector" as used herein refers to any recombinant DNA cloning vector in which a promoter to control transcription of the inserted DNA has been incorporated.

"Transcription" refers to the process whereby information contained in a nucleotide sequence of DNA is transferred to a complementary RNA sequence.

"Transfection" refers to the uptake of an expression vector by a host cell whether or not any coding sequences are, in fact, expressed. Numerous methods of transfection are known to the ordinarily skilled artisan, for example, calcium phosphate co-precipitation, liposome transfection, and electroporation. Successful transfection is generally recognized when any indication of the operation of this vector occurs within the host cell.

"Transformation" refers to the introduction of DNA into an organism so that the DNA is replicable, either as an extrachromosomal element or by chromosomal integration. Methods of transforming bacterial and eukaryotic hosts are well known in the art, many of which methods, such as nuclear injection, protoplast fusion or by calcium treatment using calcium chloride are summarized in J. Sambrook, et al., Molecular Cloning: A Laboratory Manual, (1989). Generally, when introducing DNA into Yeast the term transformation is used as opposed to the term transfection.

"Translation" as used herein refers to the process whereby the genetic information of messenger RNA (mRNA) is used to specify and direct the synthesis of a polypeptide chain.

"Vector" refers to a nucleic acid compound used for the transfection and/or transformation of cells in gene manipulation bearing polynucleotide sequences corresponding to appropriate protein molecules which, when combined with appropriate control sequences, confers specific properties on the host cell to be transfected and/or transformed. Plasmids, viruses, and bacteriophage are suitable vectors. Artificial vectors are constructed by cutting and joining DNA molecules from different sources using restriction enzymes and ligases. The term "vector" as used herein includes Recombinant DNA cloning vectors and Recombinant DNA expression vectors.

"Complementary" or "Complementarity", as used herein, refers to pairs of bases (purines and pyrimidines) that associate through hydrogen bonding in a double stranded nucleic acid. The following base pairs are complementary: guanine and cytosine; adenine and thymine; and adenine and uracil.

"Primer" refers to a nucleic acid fragment which functions as an initiating substrate for enzymatic or synthetic elongation.

"Promoter" refers to a DNA sequence which directs transcription of DNA to RNA.

"Probe" refers to a nucleic acid compound or a fragment, thereof, which hybridizes with another nucleic acid compound.

"Leader sequence" refers to a sequence of amino acids which can be enzymatically or chemically removed to produce the desired polypeptide of interest.

"Secretion signal sequence" refers to a sequence of amino acids generally present at the N-terminal region of a larger polypeptide functioning to initiate association of that polypeptide with the cell membrane compartments like endoplasmic reticulum and secretion of that polypeptide through the plasma membrane.

Wild-type human IgG4 proteins can be obtained from a variety of sources. For example, these proteins can be obtained from a cDNA library prepared from cells which express the mRNA of interest at a detectable level. Libraries can be screened with probes designed using the published DNA or protein sequence for the particular protein of interest. For example, immunoglobulin light or heavy chain constant regions are described in Adams, et al. (1980) Biochemistry 19:2711-2719; Goughet, et al. (1980) Biochemistry 19:2702-2710; Dolby, et al. (1980) Proc. Natl. Acad. Sci. USA 77:6027-6031; Rice et al. (1982) Proc. Natl. Acad. Sci. USA 79:7862-7862; Falkner, et al. (1982) Nature 298:286-288; and Morrison, et al. (1984) Ann. Rev. Immunol. 2:239-256.

Screening a cDNA or genomic library with the selected probe may be conducted using standard procedures, such as described in Sambrook et al., *Molecular Cloning: A Laboratory Manual*, Cold Spring Harbor Laboratory Press, NY (1989). An alternative means to isolate a gene encoding an immunoglobulin protein is to use PCR methodology [Sambrook et al., supra; Dieffenbach et al., *PCR Primer: A Laboratory Manual*, Cold Spring Harbor Laboratory Press, NY (1995)]. PCR primers can be designed based on published sequences.

Generally the full-length wild-type sequences cloned from a particular library can serve as a template to create the IgG4 Fc analog fragments of the present invention that retain the ability to confer a longer plasma half-life on the GLP-1 analog that is part of the fusion protein. The IgG4 Fc analog fragments can be generated using PCR techniques with primers designed to hybridize to sequences corresponding to the desired ends of the fragment. PCR primers can also be designed to create restriction enzyme sites to facilitate cloning into expression vectors.

DNA encoding the GLP-1 analogs of the present invention can be made by a variety of different methods including cloning methods like those described above as well as chemically synthesized DNA. Chemical synthesis may be attractive given the short length of the encoded peptide. The amino acid sequence for GLP-1 has been published as well as the sequence of the preproglucagon gene. [Lopez, et al. (1983) Proc. Natl. Acad. Sci., USA 80:5485-5489; Bell, et al. (1983) Nature, 302:716-718; Heinrich, G., et al. (1984) Endocrinol, 115:2176-2181; Ghiglione, M., et al. 91984) Diabetologia 27:599-600]. Thus, primers can be designed based on the native sequence to generate DNA encoding the GLP-1 analogs described herein.

The gene encoding a fusion protein can then be constructed by ligating DNA encoding a GLP-1 analog in-frame to DNA encoding the IgG Fc proteins described herein. The DNA encoding wild-type GLP-1 and IgG4 Fc fragments can be mutated either before ligation or in the context of a CDNA encoding an entire fusion protein. A variety of mutagenesis techniques are well known in the art. The gene encoding the GLP-1 analog and the gene encoding the IgG4 Fc analog protein can also be joined in-frame via DNA encoding a G-rich linker peptide. A preferred DNA sequence encoding one of the preferred heterologous fusion proteins of the present invention, Gly$^8$-Glu$^{22}$-Gly$^{36}$-GLP-1(7-37)-1L-IgG4 (S228P, F234A, L235A, des K), is provided as SEQ ID NO:20:

(SEQ ID NO:20)
CACGGCGAGGGCACCTTCACCTCCGACGTGTCCTCCTATCTCGAGGAGCA

GGCCGCCAAGGAATTCATCGCCTGGCTGGTGAAGGGCGGCGGCGGTGGTG

-continued
GTGGCTCCGGAGGCGGCGGCTCTGGTGGCGGTGGCAGCGCTGAGTCCAAA

TATGGTCCCCCATGCCCACCCTGCCCAGCACCTGAGGCCGCCGGGGGACC

ATCAGTCTTCCTGTTCCCCCCAAAACCCAAGGACACTCTCATGATCTCCC

GGACCCCTGAGGTCACGTGCGTGGTGGTGGACGTGAGCCAGGAAGACCCC

GAGGTCCAGTTCAACTGGTACGTGGATGGCGTGGAGGTGCATAATGCCAA

GACAAAGCCGCGGGAGGAGCAGTTCAACAGCACGTACCGTGTGGTCAGCG

TCCTCACCGTCCTGCACCAGGACTGGCTGAACGGCAAGGAGTACAAGTGC

AAGGTCTCCAACAAAGGCCTCCCGTCCTCCATCGAGAAAACCATCTCCAA

AGCCAAAGGGCAGCCCCGAGAGCCACAGGTGTACACCCTGCCCCCATCCC

AGGAGGAGATGACCAAGAACCAGGTCAGCGTGACCTGCCTGGTCAAAGGC

TTCTACCCCAGCGACATCGCCGTGGAGTGGGAAAGCAATGGGCAGCCGGA

GAACAACTACAAGACCACGCCTCCCGTGCTGGACTCCGACGGCTCCTTCT

TCCTCTACAGCAGGCTAACCGTGGACAAGAGCAGGTGGCAGGAGGGGAAT

GTCTTCTCATGCTCCGTGATGCATGAGGCTCTGCACAACCACTACACACA

GAAGAGCCTCTCCCTGTCTCTGGGT

Host cells are transfected or transformed with expression or cloning vectors described herein for heterologous fusion protein production and cultured in conventional nutrient media modified as appropriate for inducing promoters, selecting transformants, or amplifying the genes encoding the desired sequences. The culture conditions, such as media, temperature, pH and the like, can be selected by the skilled artisan without undue experimentation. In general, principles, protocols, and practical techniques for maximizing the productivity of cell cultures can be found in *Mammalian Cell Biotechnology: A Practical Approach*, M. Butler, ed. (IRL Press, 1991) and Sambrook, et al., supra. Methods of transfection are known to the ordinarily skilled artisan, for example, CaPO$_4$ and electroporation. General aspects of mammalian cell host system transformations have been described in U.S. Pat. No. 4,399,216. Transformations into yeast are typically carried out according to the method of van Solingen et al., *J Bact.* 130 (2): 946-7 (1977) and Hsiao et al., *Proc. Natl. Acad. Sci. USA* 76 (8): 3829-33 (1979). However, other methods for introducing DNA into cells, such as by nuclear microinjection, electroporation, bacterial protoplast fusion with intact cells, or polycations, e.g., polybrene or polyornithine, may also be used. For various techniques for transforming mammalian cells, see Keown, et al., *Methods in Enzymology* 185: 527-37 (1990) and Mansour, et al., *Nature* 336 (6197): 348-52 (1988).

Suitable host cells for cloning or expressing the nucleic acid (e.g., DNA) in the vectors herein include yeast or higher eukaryote cells.

Eukaryotic microbes such as filamentous fungi or yeast are suitable cloning or expression hosts for fusion protein vectors. *Saccharomyces cerevisiae* is a commonly used lower eukaryotic host microorganism. Others include *Schizosaccharomyces pombe* [Beach and Nurse, *Nature* 290: 140-3 (1981); EP 139,383 published 2 May 1995]; *Muyveromyces* hosts [U.S. Pat. No. 4,943,529; Fleer, et al., *Bio/Technology* 9 (10): 968-75 (1991)] such as, e.g., *K. lactis* (MW98-8C, CBS683, CBS4574) [de Louvencourt et al., *J. Bacteriol.* 154 (2): 737-42 (1983)]; *K. fiagilis* (ATCC 12,424), *K. bulgaricus* (ATCC 16,045), *K. wickeramii* (ATCC 24,178), *K. waltii* (ATCC 56,500), *K. drosophilarum* (ATCC 36.906) [Van den Berg et al., *Bio/Technology* 8 (2): 135-9 (1990)]; *K. thermo-* toierans, and *K. marxianus; yarrowia* (EP 402,226); *Pichia pastoris* (EP 183,070) [Sreekrishna et al., *J. Basic Microbiol.* 28 (4): 265-78 (1988)]; Candid; *Trichoderma reesia* (EP 244, 234); *Neurospora crassa* [Case, et al., *Proc. Natl. Acad Sci. USA* 76 (10): 5259-63 (1979)]; *Schwanniomyces* such as *Schwanniomyces occidentulis* (EP 394,538 published 31 Oct. 1990); and filamentous fungi such as, e.g., *Neurospora, Penicillium, Tolypocladium* (WO 91/00357 published 10 Jan. 1991), and *Aspergillus* hosts such as *A. nidulans* [Ballance et al., *Biochem. Biophys. Res. Comm.* 112 (1): 284-9 (1983)]; Tilbum, et al., *Gene* 26 (2-3): 205-21 (1983); Yelton, et al., *Proc. Natl. Acad. Sci. USA* 81 (5):1470-4 (1984)] and *A. niger* [Kelly and Hynes, EMBO J. 4 (2): 475-9 (1985)]. Methylotropic yeasts are selected from the genera consisting of *Hansenula, Candida, Kloeckera, Pichia, Saccharomyces, Torulopsis*, and *Rhodotoruia*. A list of specific species that are exemplary of this class of yeast may be found in C. Antony, *The Biochemistry of Methylotrophs* 269 (1982).

Suitable host cells for the expression of the fusion proteins of the present invention are derived from multicellular organisms. Examples of invertebrate cells include insect cells such as *Drosophila* S2 and *Spodoptera* Sp, *Spodoptera* high5 as well as plant cells. Examples of useful mammalian host cell lines include NSO myeloma cells, Chinese hamster ovary (CHO), SP2, and COS cells. More specific examples include monkey kidney CV1 line transformed by SV40 (COS-7, ATCC CRL 1651); human embryonic kidney line [293 or 293 cells subcloned for growth in suspension culture, Graham, et al., *J. Gen Virol.*, 36 (1): 59-74 (1977)]; Chinese hamster ovary cells/-DHFR [CHO, Urlaub and Chasin, *Proc. Natl. Acad. Sci. USA,* 77 (7): 4216-20 (1980)]; mouse sertoli cells [TM4, Mather, *Biol. Reprod.* 23 (1):243-52 (1980)]; human lung cells (W138. ATCC CCL 75); human liver cells (Hep G2, HB 8065); and mouse mammary tumor (MMT 060562, ATCC CCL51). A preferred cell line for production of the Fc fusion proteins of the present invention is the NS0 myeloma cell line available from the European Collection of Cell Cultures (ECACC, catalog #85110503) and described in Galfre, G. and Milstein, C. ((1981) Methods in Enzymology 73 (13): 3-46; and Preparation of Monoclonal Antibodies: Strategies and Procedures, Academic Press, N.Y., N.Y.).

The fusion proteins of the present invention may be recombinantly produced directly, or as a protein having a signal sequence or other additional sequences which create a specific cleavage site at the N-terminus of the mature fusion protein. In general, the signal sequence may be a component of the vector, or it may be a part of the fusion protein-encoding DNA that is inserted into the vector. For yeast secretion the signal sequence may be, e.g., the yeast invertase leader, alpha factor leader (including *Saccharomyces* and *Kluyveromyces* cc-factor leaders, the latter described in U.S. Pat. No. 5,010, 182), or acid phosphatase leader, the *C. albicans* glucoamylase leader (EP 362,179), or the signal described in WO 90/13646. In mammalian cell expression, mammalian signal sequences may be used to direct secretion of the protein, such as signal sequences from secreted polypeptides of the same or related species as well as viral secretory leaders.

Both expression and cloning vectors contain a nucleic acid sequence that enables the vector to replicate in one or more selected host cells. Expression and cloning vectors will typically contain a selection gene, also termed a selectable marker. Typical selection genes encode proteins that (a) confer resistance to antibiotics or other toxins, e.g., neomycin, methotrexate, or tetracycline, (b) complement autotrophic deficiencies, or (c) supply critical nutrients not available from complex media, e.g., the gene encoding D-alanine racemase for *Bacilli*.

An example of suitable selectable markers for mammalian cells are those that enable the identification of cells competent to take up the fusion protein-encoding nucleic acid, such as DHFR or thymidine kinase. An appropriate host cell when wild-type DHFR is employed is the CHO cell line deficient in DHFR activity, prepared and propagated as described [Urlaub and Chasin, *Proc. Natl. Acad. Sci. USA,* 77 (7): 4216-20 (1980)]. A suitable selection gene for use in yeast is the trp1 gene present in the yeast plasmid YRp7 [Stinchcomb, et al., *Nature* 282 (5734): 39-43 (1979); Kingsman, et al., *Gene* 7(2): 141-52 (1979); Tschumper, et al., Gene 10 (2): 157-66 (1980)]. The trp1 gene provides a selection marker for a mutant strain of yeast lacking the ability to grow in tryptophan, for example, ATCC No. 44076 or PEPC1 [Jones, *Genetics* 85: 23-33 (1977)].

Expression and cloning vectors usually contain a promoter operably linked to the fusion protein-encoding nucleic acid sequence to direct MRNA synthesis. Promoters recognized by a variety of potential host cells are well known. Examples of suitable promoting sequences for use with yeast hosts include the promoters for 3-phosphoglycerate kinase [Hitzeman, et al., *J. Biol. Chem.* 255 (24): 12073-80 (1980)] or other glycolytic enzymes [Hess et al., *J. Adv. Enzyme Reg.* 7: 149 (1968); Holland, *Biochemistry* 17 (23): 4900-7 (1978)], such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657. Transcription of fusion protein-encoding mRNA from vectors in mammalian host cells may be controlled, for example, by promoters obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus and Simian Virus 40 (SV40), from heterologous mammalian promoters, e.g., the actin promoter or an immunoglobulin promoter, and from heat-shock promoters, provided such promoters are compatible with the host cell systems.

Transcription of a polynucleotide encoding a fusion protein by higher eukaryotes may be increased by inserting an enhancer sequence into the vector. Enhancers are cis-acting elements of DNA, usually about from 10 to 300 bp, that act on a promoter to increase its transcription. Many enhancer sequences are now known from mammalian genes (globin, elastase, albumin, a-ketoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. The enhancer may be spliced into the vector at a position 5' or 3' to the fusion protein coding sequence but is preferably located at a site 5' from the promoter.

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and occasionally 3' untranslated regions of eukaryotic or viral DNAs or cDNAs. These regions contain nucleotide segments transcribed as polyadenylated fragments in the untranslated portion of the mRNA encoding the fusion protein.

Various forms of a fusion protein may be recovered from culture medium or from host cell lysates. If membrane-bound, it can be released from the membrane using a suitable detergent solution (e.g., Triton-X 100) or by enzymatic cleavage. Cells employed in expression of a fusion protein can be disrupted by various physical or chemical means, such as freeze-thaw cycling, sonication, mechanical disruption, or cell lysing agents.

Once the heterologous fusion proteins of the present invention are expressed in the appropriate host cell, the analogs can be isolated and purified. The following procedures are exemplary of suitable purification procedures: fractionation on carboxymethyl cellulose; gel filtration such as Sephadex G-75; anion exchange resin such as DEAE or Mono-Q; cation exchange such as CM or Mono-S; metal chelating columns to bind epitope-tagged forms of the polypeptide; reversed-phase HPLC; chromatofocusing; silica gel; ethanol precipitation; and ammonium sulfate precipitation.

Various methods of protein purification may be employed and such methods are known in the art and described, for example, in Deutscher, *Methods in Enzymology* 182: 83-9 (1990) and Scopes, *Protein Purification: Principles and Practice*, Springer-Verlag, NY (1982). The purification step(s) selected will depend on the nature of the production process used and the particular fusion protein produced. For example, fusion proteins comprising an Fc fragment can be effectively purified using a Protein A or Protein G affinity matrix. Low or high pH buffers can be used to elute the fusion protein from the affinity matrix. Mild elution conditions will aid in preventing irreversible denaturation of the fusion protein.

The heterologous fusion proteins of the present invention may be formulated with one or more excipients. The fusion proteins of the present invention may be combined with a pharmaceutically acceptable buffer, and the pH adjusted to provide acceptable stability, and a pH acceptable for administration such as parenteral administration. Optionally, one or more pharmaceutically-acceptable anti-microbial agents may be added. Meta-cresol and phenol are preferred pharmaceutically-acceptable microbial agents. One or more pharmaceutically-acceptable salts may be added to adjust the ionic strength or tonicity. One or more excipients may be added to further adjust the isotonicity of the formulation. Glycerin is an example of an isotonicity-adjusting excipient. Pharmaceutically acceptable means suitable for administration to a human or other animal and thus, does not contain toxic elements or undesirable contaminants and does not interfere with the activity of the active compounds therein.

The heterologous fusion proteins of the present invention may be formulated as a solution formulation or as a lyophilized powder that can be reconstituted with an appropriate diluent. A lyophilized dosage form is one in which the fusion protein is stable, with or without buffering capacity to maintain the pH of the solution over the intended in-use shelf-life of the reconstituted product. It is preferable that the solution comprising the heterologous fusion proteins discussed herein before lyphilization be substantially isotonic to enable formation of isotonic solutions after reconstitution.

A pharmaceutically-acceptable salt form of the heterologous fusion proteins of the present invention are within the scope of the invention. Acids commonly employed to form acid addition salts are inorganic acids such as hydrochloric acid, hydrobromic acid, hydriodic acid, sulfuric acid, phosphoric acid, and the like, and organic acids such as p-toluenesulfonic acid, methanesulfonic acid, oxalic acid, p-bromophenyl-sulfonic acid, carbonic acid, succinic acid, citric acid, benzoic acid, acetic acid, and the like. Preferred acid addition salts are those formed with mineral acids such as hydrochloric acid and hydrobromic acid.

Base addition salts include those derived from inorganic bases, such as ammonium or alkali or alkaline earth metal hydroxides, carbonates, bicarbonates, and the like. Such bases useful in preparing the salts of this invention thus include sodium hydroxide, potassium hydroxide, ammonium hydroxide, potassium carbonate, and the like.

The heterologous fusion proteins of the present invention have biological activity. Biological activity refers to the ability of the fusion protein to bind to and activate the GLP-1 receptor in vivo and elicit a response. Responses include, but are not limited to, secretion of insulin, suppression of glucagon, inhibition of appetite, weight loss, induction of satiety, inhibition of apoptosis, induction of pancreatic beta cell proliferation, and differentiation of pancreatic beta cells. A representative number of GLP-1 fusion proteins were tested for in vitro as well as in vivo activity. Examples 1 and 2 provide in vitro activity based on the ability of the fusion protein to interact with and activate the human GLP-1 receptor. In both sets of experiments, HEK293 cells over-expressing the human GLP-1 receptor were used. Activation of the GLP-1 receptor in these cells causes adenylyl cyclase activation which in turn induces expression of a reporter gene driven by a cyclic AMP response element (CRE). Example 1 (table 1) provides data wherein the reporter gene is beta lactamase, and example 2 (table 2) provides data wherein the reporter gene is luciferase. Example 3 provides data generated after administration of one of the heterologous fusion proteins of the present invention to rats. Together the data show that the fusion proteins are able to bind to and activate the GLP-1 receptor and appear more potent in vitro than $Val^8$-GLP-1(7-37)OH. In addition, the data generated in rats indicate the fusion proteins are active in vivo and have a longer half-life than native GLP-1.

Administration of the heterogeneous fusion proteins may be via any route known to be effective by the physician of ordinary skill. Peripheral parenteral is one such method. Parenteral administration is commonly understood in the medical literature as the injection of a dosage form into the body by a sterile syringe or some other mechanical device such as an infusion pump. Peripheral parenteral routes can include intravenous, intramuscular, subcutaneous, and intraperitoneal routes of administration.

The heterologous fusion proteins of the present invention may also be amenable to administration by oral, rectal, nasal, or lower respiratory routes, which are non-parenteral routes. Of these non-parenteral routes, the lower respiratory route and the oral route are preferred.

The fusion proteins of the present invention can be used to treat a wide variety of diseases and conditions. The fusion proteins of the present invention primarily exert their biological effects by acting at a receptor referred to as the "GLP-1 receptor." Subjects with diseases and/or conditions that respond favorably to GLP-1 receptor stimulation or to the administration of GLP-1 compounds can therefore be treated with the GLP-1 fusion proteins of the present invention. These subjects are said to "be in need of treatment with GLP-1 compounds" or "in need of GLP-1 receptor stimulation". Included are subjects with non-insulin dependent diabetes, insulin dependent diabetes, stroke (see WO 00/16797), myocardial infarction (see WO 98/08531), obesity (see WO 98/19698), catabolic changes after surgery (see U.S. Pat. No. 6,006,753), functional dyspepsia and irritable bowel syndrome (see WO 99/64060). Also included are subjects requiring prophylactic treatment with a GLP-1 compound, e.g., subjects at risk for developing non-insulin dependent diabetes (see WO 00/07617). Subjects with impaired glucose tolerance or impaired fasting glucose, subjects whose body weight is about 25% above normal body weight for the subject's height and body build, subjects with a partial pancreatectomy, subjects having one or more parents with non-insulin dependent diabetes, subjects who have had gestational diabetes and subjects who have had acute or chronic pancreatitis are at risk for developing non-insulin dependent diabetes.

An effective amount of the GLP-1-Fc fusion proteins described herein is the quantity which results in a desired therapeutic and/or prophylactic effect without causing unacceptable side-effects when administered to a subject in need of GLP-1 receptor stimulation. A "desired therapeutic effect" includes one or more of the following: 1) an amelioration of the symptom(s) associated with the disease or condition; 2) a delay in the onset of symptoms associated with the disease or condition; 3) increased longevity compared with the absence of the treatment; and 4) greater quality of life compared with the absence of the treatment. For example, an "effective amount" of a GLP-1-Fc fusion protein for the treatment of diabetes is the quantity that would result in greater control of blood glucose concentration than in the absence of treatment, thereby resulting in a delay in the onset of diabetic complications such as retinopathy, neuropathy or kidney disease. An "effective amount" of a GLP-1-Fc fusion protein for the prevention of diabetes is the quantity that would delay, compared with the absence of treatment, the onset of elevated blood glucose levels that require treatment with anti-hypoglycaemic drugs such as sulfonyl ureas, thiazolidinediones, insulin and/or bisguanidines.

The dose of fusion protein effective to normalize a patient's blood glucose will depend on a number of factors, among which are included, without limitation, the subject's sex, weight and age, the severity of inability to regulate blood glucose, the route of administration and bioavailability, the pharmacokinetic profile of the fusion protein, the potency, and the formulation. Doses may be in the range of 0.01 to 1 mg/kg body weight, preferably in the range of 0.05 to 0.5 mg/kg body weight.

It is preferable that the fusion proteins of the present invention be administered either once every two weeks or once a week. Depending on the disease being treated, it may be necessary to administer the fusion protein more frequently such as two to three time per week.

The present invention will now be described only by way of non-limiting example with reference to the following Examples.

EXAMPLES

Example 1

In Vitro GLP-1 Receptor Activation Assay

HEK-293 cells expressing the human GLP-1 receptor, using a CRE-BLAM system, are seeded at 20,000 to 40,000 cells/well/100 µl DMEM medium with 10% FBS into a poly-d-lysine coated 96 well black, clear-bottom plate. The day after seeding, the medium is flicked off and 80 µl plasma-free DMEM medium is added. On the third day after seeding, 20 µl of plasma-free DMEM medium with 0.5% BSA containing different concentrations of various GLP-1-Fc heterologous fusion protein is added to each well to generate a dose response curve. Generally, fourteen dilutions containing from 3 nanomolar to 30 nanomolar or heterologous GLP-1 Fc fusion protein are used to generate a dose response curve from which $EC_{50}$ values can be determined. After 5 hours of incubation with the fusion protein, 20 µl of β-lactamase substrate (CCF2/AM, PanVera LLC) is added and incubation continued for 1 hour at which time fluorescence is determined on a cytofluor. The assay is further described in Zlokarnik, et al. (1998), *Science,* 278:84-88. Various GLP-1-Fc fusion proteins are tested and $EC_{50}$ values are represented in Table 1. The values are relative to values determined for $Val^8$-GLP-1 (7-37)OH which is run as an internal control with every experiment.

TABLE 1

| Compound | Activity | Std. Dev. |
|---|---|---|
| $Val^8$-GLP-1: | 100% | |
| $Gly^8$-$Glu^{22}$-GLP-1(7-37)-2L-IgG4 (S228P, F234A, L235A): | 301% | 99 |
| Gly8-$Glu^{22}$-GLP-1(7-37)-1.5L-IgG4 (S228P, F234A, L235A): | 314% | 45 |
| $Gly^8$-$Glu^{22}$-GLP-1(7-37)-1L-IgG4 (S228P, F234A, L235A): | 468% | 120 |
| $Gly^8$-$Glu^{22}$-$Gly^{36}$-GLP-1(7-37)-2L-IgG4 (S228P, F234A, L235A): | 441% | 35 |

Example 2

In Vitro GLP-1 Receptor Activation Assay

HEK-293 cells stably expressing the human GLP-1 receptor, using a CRE-Luciferase system, are seeded at 30,000 cells/well/80 µl low serum DMEM F12 medium into 96 well plates. The day after seeding, 20 µl aliquots of test protein dissolved in 0.5% BSA are mixed and incubated with the cells for 5 hours. Generally 12 dilutions containing from 3 pM to 3 nM are prepared at a 5× concentration for each test protein before addition to the cells to generate a dose response curve from which $EC_{50}$ values are determined. After incubation, 100 µl of Luciferase reagent is added directly to each plate and mixed gently for 2 minutes. Plates are placed in a Tri-lux luminometer and light output resulting from luciferase expression is calculated. Various GLP-1-Fc fusion proteins are tested and $EC_{50}$ values are represented in Table 2. The values are relative to values determined for $Val^8$-GLP-1(7-37)OH which is run as an internal control with every experiment. Because the fusion proteins tested below are dimers, values are corrected taking into account a 2-fold difference in molarity.

TABLE 2

| Compound | Activity | Std. Dev. |
|---|---|---|
| $Val^8$-GLP-1: | 100% | |
| $Gly^8$-$Glu^{22}$-GLP-1(7-37)-2L-IgG4 (S228P, F234A, L235A): | 535% | 240 |
| $Gly^8$-$Glu^{22}$-GLP-1(7-37)-1.5L-IgG4 (S228P, F234A, L235A): | 595% | 43 |
| $Gly^8$-$Glu^{22}$-GLP-1(7-37)-1L-IgG4 (S228P, F234A, L235A): | 1119% | 128 |
| $Gly^8$-$Glu^{22}$-$Gly^{36}$-GLP-1(7-37)-2L-IgG4 (S228P, F234A, L235A): | 398% | 62 |
| $Gly^8$-$Glu^{22}$-$Gly^{36}$-GLP-1(7-37)-1L-IgG4 (S228P, F234A, L235A): | 417% | 140 |

Example 3

Intravenous Glucose Tolerance Test in Rats

The Fc fusion protein, Gly$^8$-Glu$^{22}$-Gly$^{36}$-GLP-1(7-37)-L-IgG4 (S228P, F234A, L235A), is evaluated in an intravenous glucose tolerance test (IVGTT) in rats. At least four rats are included into each of three groups. Group I receives vehicle (table 3), Group II receives 1.79 mg/kg of Gly$^8$-Glu$^{22}$-Gly$^{36}$-GLP-1(7-37)-L-IgG4 (S228P, F234A, L235A) as a single subcutaneous injection (table 4), and Group III receives 0.179 mg/kg of Gly$^8$-Glu$^{22}$-Gly$^{36}$-GLP-1(7-37)-L-IgG4 (S228P, F234A, L235A) as a single subcutaneous injection (table 5). Rats are subcutaneously injected the morning of Day 1. Twenty-four hours following the first injection, 1 µL of glucose (D50) per gram rat body weight is infused as a bolus. Blood samples are taken at 2, 4, 6, 10, 20, and 30 minutes following the bolus infusion of glucose.

TABLE 3

| Vehicle: Insulin AUC (ng*min/mL) | Rat 1 | Rat 2 | Rat 3 | Rat 4 | Rat 5 | Average | SEM |
|---|---|---|---|---|---|---|---|
| 0-2 | 11 | 9.4 | 7 | 11 | 9.6 | | |
| 2-4 | 18.1 | 9.7 | 5.6 | 10.6 | 8.8 | | |
| 4-6 | 13.4 | 7 | 3.4 | 9.6 | 5.9 | | |
| 6-10 | 7.9 | 3.5 | 2.5 | 6 | 2.9 | | |
| 10-20 | 3.7 | 3 | 2.4 | 3 | 2.4 | | |
| 20-30 | 2 | 0 | 0 | 0 | 2.4 | | |
| sum | 56.1 | 32.6 | 20.9 | 40.2 | 32 | 36.4 | 5.8 |

TABLE 4

| GLP-1-Fc (1.79 mg/kg) Insulin AUC (ng*min/mL) | Rat 1 | Rat 2 | Rat 3 | Rat 4 | Rat 5 | Average | SEM |
|---|---|---|---|---|---|---|---|
| 0-2 | 12.3 | 17.4 | 16 | 14 | 13 | | |
| 2-4 | 21.9 | 13.3 | 13.2 | 13.9 | 13.6 | | |
| 4-6 | 16.8 | 6.5 | 9.8 | 11.1 | 11.7 | | |
| 6-10 | 7.6 | 3.8 | 9.2 | 5.8 | 7.4 | | |
| 10-20 | 3 | 0 | 0 | 3.2 | 5.6 | | |
| 20-30 | 0 | 0 | 0 | 0 | 0 | | |
| sum | 61.6 | 41 | 48.2 | 48 | 51.3 | 50 | 3.4 |

TABLE 5

| GLP-1-Fc (0.179 mg/kg) Insulin AUC (ng*min/mL) | Rat 1 | Rat 2 | Rat 3 | Rat 4 | Average | SEM |
|---|---|---|---|---|---|---|
| 0-2 | 14.4 | 29.2 | 25.4 | 23.2 | | |
| 2-4 | 13.8 | 26.3 | 21.2 | 21.8 | | |
| 4-6 | 11.2 | 19.4 | 16.4 | 15.7 | | |
| 6-10 | 6.4 | 10.6 | 10.5 | 8 | | |
| 10-20 | 3.6 | 5.8 | 5.2 | 5 | | |
| 20-30 | 0 | 0 | 0 | 0 | | |
| sum | 49.4 | 91.3 | 78.7 | 73.7 | 78.7 | 8.7 |

Example 4

Pharmacokinetic Study Following a Single Subcutaneous Injection to Cynomolgus Monkeys A study is performed to characterize the pharmacokinetics (PK) of the Fc fusion protein, Gly$^8$-Glu$^{22}$-Gly$^{36}$-GLP-1(7-37)-L-IgG4 (S228P, F234A, L235A), when administered as a 0.1 mg/kg by subcutaneous (SC) injection to male cynomolgus monkeys. RIA antibody is specific for the middle portion of GLP. ELISA uses an N-terminus specific capture antibody and an Fc specific detection antibody. Resulting plasma concentrations from both the ELISA and the RIA are used to determine the represented pharmacokinetic parameter values.

A representation of the resulting PK parameter values is summarized in table 6. Single-dose SC PK from the RIA is associated with a mean $C_{max}$ of 446.7 ng/mL with a corresponding $T_{max}$ of 17.3 hours. The mean elimination half-life is approximately 79.3 hours (3.3 days). The PK from the ELISA is associated with a mean $C_{max}$ of 292.2 ng/mL with a corresponding $T_{max}$ of 16.7 hours. The mean elimination half-life is approximately is 51.6 hours (2.2 days).

TABLE 6

| Dose (mg/kg) | Animal # | $C_{max}^a$ (ng/mL) | $T_{max}^b$ (h) | $AUC_{0-\infty}^c$ (ng*h/mL) | $t_{1/2}^d$ (h) | $CL/F^e$ (mL/h/kg) | $Vss/F^f$ (mL/kg) |
|---|---|---|---|---|---|---|---|
| | | | | RIA | | | |
| 0.1 | 96051 | 461.0 | 4.0 | 37770.5 | 81.0 | 2.7 | 309.2 |
| | 96071 | 430.0 | 24.0 | 43150.2 | 74.2 | 2.3 | 248.1 |
| | 96091 | 449.0 | 24.0 | 62271.1 | 82.9 | 1.6 | 191.9 |
| RIA | Mean | 446.7 | 17.3 | 47730.6 | 79.3 | 2.2 | 249.8 |
| | SD | 15.6 | 11.5 | 12876.5 | 4.5 | 0.5 | 58.7 |
| | | | | ELISA | | | |
| | 96051 | 315.4 | 2.0 | 9062.3 | 55.2 | 11.0 | 879.4 |
| | 96071 | 289.4 | 24.0 | 16653.0 | 50.3 | 6.0 | 436.0 |
| | 96091 | 271.9 | 24.0 | 19907.4 | 49.3 | 5.0 | 357.0 |

TABLE 6-continued

| Dose (mg/kg) | Animal # | $C_{max}^a$ (ng/mL) | $T_{max}^b$ (h) | $AUC_{0-\infty}^c$ (ng*h/mL) | $t_{1/2}^d$ (h) | $CL/F^e$ (mL/h/kg) | $Vss/F^f$ (mL/kg) |
|---|---|---|---|---|---|---|---|
| ELISA | Mean | 292.2 | 16.7 | 15207.6 | 51.6 | 7.3 | 557.5 |
|  | SD | 21.9 | 12.7 | 5565.2 | 3.2 | 3.2 | 281.6 |

[a]Maximum observed plasma concentration.
[b]Time of maximum observed plasma concentration.
[c]Area under the plasma concentration-time curve measured from 0 to infinity.
[d]Elimination half-life.
[e]Total body clearance as a function of bioavailability.
[f]Volume of distribution as a function of bioavailability.
SD = Standard deviation.

Example 5

Assessment of the Potential Formation of Antibodies Following Repeat Subcutaneous Injections Designated serum samples from cynomolgus monkeys are tested for the formation of antibodies against $Gly^8$-$Glu^{22}$-$Gly^{36}$-GLP-1(7-37)-L-IgG4 (S228P, F234A, L235A) using a direct ELISA format. Microtiter plates are coated with $Gly^8$-$Glu^{22}$-$Gly^{36}$-GLP-1(7-37)-L-IgG4 (S228P, F234A, L235A) at a 0.1 μg/mL concentration. Monkey serum samples are diluted 50, 500, 1000 and 5000 fold into blocking solution, and 0.05 mL sample/well are incubated approximately one hour. Secondary antibody, Goat <Human Fab'2>-Peroxidase (with 75% cross reactivity to human), is diluted 10,000 fold into block and added at 0.05 mL/well and incubated approximately one hour. Color development using tetramethylbenzidine (TMB) substrate is read at an optical density of 450 nm-630 nm. Duplicate readings are averaged. A GLP-1 antibody was used as a positive control and goat<rabbit> (H+L)-Peroxidase conjugate is the secondary used for detection. Point serum samples are collected prior to dosing, at 24 hours following the second dose, and 168 hours following the first and second SC dose for an evaluation of potential immunogenicity. The presence of antibody titers to G8E22-CEX-L-hIgG4 is interpreted by comparison to predose serum samples and positive control. A representation of the results is presented in table 7.

TABLE 7

| | Dose 1 Animal# | | | | | | | | |
|---|---|---|---|---|---|---|---|---|---|
| | Positive Control | IO7774 | | IO7777 | | IO7779 | | IO7780 | |
| | | Sample Time: | | | | | | | |
| | | Predose | 168 h | Predose | 168 h | Predose | 168 h | Predose | 168 h |
| 50x | 2.854 | 0.268 | 0.268 | 0.160 | 0.128 | 0.144 | 0.152 | 0.264 | 0.224 |
| 500x | 2.270 | 0.117 | 0.133 | 0.052 | 0.069 | 0.065 | 0.061 | 0.067 | 0.061 |
| 1000x | 1.610 | 0.091 | 0.075 | 0.034 | 0.051 | 0.047 | 0.045 | 0.138 | 0.049 |
| 5000x | 0.525 | 0.056 | 0.048 | 0.032 | 0.037 | 0.029 | 0.033 | 0.051 | 0.039 |
| | Dose 2 Animal# | | | | | | | | |
| | Positive Control | IO7774 | | IO7777 | | IO7779 | | IO7780 | |
| | | Sample Time: | | | | | | | |
| | | Predose | 24 h | Predose | 24 h | Predose | 24 h | Predose | 24 h |
| 50x | 3.056 | 0.298 | 0.231 | 0.164 | 0.159 | 0.227 | 0.176 | 0.211 | 0.192 |
| 500x | 2.247 | 0.120 | 0.119 | 0.048 | 0.045 | 0.061 | 0.060 | 0.056 | 0.057 |
| 1000x | 1.673 | 0.090 | 0.086 | 0.039 | 0.041 | 0.046 | 0.045 | 0.043 | 0.048 |
| 5000x | 0.534 | 0.039 | 0.042 | 0.030 | 0.034 | 0.033 | 0.036 | 0.033 | 0.034 |
| | Dose 2 Animal# | | | | | | | | |
| | Positive Control | IO7774 | | IO7777 | | IO7779 | | IO7780 | |
| | | Sample Time: | | | | | | | |
| | | Predose | 168 h | Predose | 168 h | Predose | 168 h | Predose | 168 h |
| 50x | 3.075 | 0.413 | 0.270 | 0.174 | 0.182 | 0.185 | 0.190 | 0.224 | 0.191 |
| 500x | 2.173 | 0.097 | 0.103 | 0.042 | 0.051 | 0.056 | 0.057 | 0.048 | 0.053 |
| 1000x | 1.510 | 0.066 | 0.067 | 0.038 | 0.040 | 0.037 | 0.046 | 0.043 | 0.043 |
| 5000x | 0.474 | 0.042 | 0.042 | 0.033 | 0.046 | 0.033 | 0.033 | 0.036 | 0.041 |

Example 6

Pharmacodynamic Study Following a Single Subcutaneously Injection to Cynomolgus Monkeys in the Fasting State and During a Graded Intravenous Glucose Infusion In Phase 1 (Study Day 1) a subcutaneous injection of vehicle is administered. A graded intravenous glucose (20% dextrose) infusion of 5, 10, and 25 mg/kg/min is then administered immediately after the vehicle injection. In Phase 2 (Study Day 3), a subcutaneous injection of a GLP-1 fusion protein (0.1 mg/kg) is administered. In Phase 3, a graded intravenous glucose infusion is performed approximately 96 hours following the GLP-1 fusion injection.

Graded intravenous glucose infusion procedures are conducted in sedated monkeys after a 16-hr overnight fast. For both intravenous glucose infusions, baseline samples will be drawn every 10 min for 20 min to define baseline. A stepped-up glucose infusion is initiated at +20 min at a rate of 5 mg/kg/min, followed by infusions of 10 mg/kg/min, and 25 mg/kg/min. Each infusion rate is administered for a period of 20 minutes. Blood samples are taken at 10 minute intervals for measurement of glucose, insulin, and glucagon. Approximately 1.0 mL of blood is collected at −20, −10 min, 0 pre-glucose infusions, and at 10, 20, 30, 40, 50, and 60 minutes following glucose infusion for Phases 1 and 3.

A representation of the data are shown in table 8.

TABLE 8

| Group | Animal | AUC (min*mg/dL) | Group | Animal | AUC (min*mg/dL) |
|---|---|---|---|---|---|
| Glucose AUC | | | | | |
| GLP-Fc | 9423 | 7447 | vehicle | 9423 | 8077 |
| | 9424 | 7470 | | 9424 | 15006 |
| | 9510 | 5153 | | 9510 | 7116 |
| | 9513 | 6303 | | 9513 | 7459 |
| | 9516 | 5413 | | 9516 | 8728 |
| | 9530 | 5240 | | 9530 | 7863 |
| | | | | N | 6 |
| | Mean | 6171 | | Mean | 9041 |
| | SD | 1078 | | SD | 2973 |
| | SE | 440 | | SE | 1214 |
| Insulin AUC | | | | | |
| GLP-Fc | 9423 | 129 | vehicle | 9423 | 38 |
| | 9424 | 138 | | 9424 | 29 |
| | 9510 | 357 | | 9510 | 69 |
| | 9513 | 161 | | 9513 | 64 |
| | 9516 | 376 | | 9516 | 38 |
| | 9530 | 215 | | 9530 | 68 |
| | Mean | 229 | | Mean | 51 |
| | SD | 111 | | SD | 18 |
| | SE | 45 | | SE | 7 |

Glucagon levels were not statistically different between the vehicle and the GLP-1 fusion protein dosed monkeys.

Example 7

Pharmacodynamic Study Following Single Subcutaneously Injections of Three Different Doses to Rats in the Fasting State and During a Graded Intravenous Glucose Infusion Chronically cannulated rats are assigned to either vehicle control (saline) or one of 3 treatment groups (GLP-1 fusion protein; 0.0179 mg/kg, 0.179 mg/kg, or 1.79 mg/kg). The GLP-1 fusion protein and vehicle are administered via subcutaneous injection. Twenty-four hours after treatment, overnight fasted (16 h) rats are subjected to a graded intravenous glucose infusion test. The graded glucose infusion test consists of a baseline saline infusion period (20 min), followed by two 30 min glucose infusion phases at 5 and 15 mg/kg/min, respectively. Plasma samples are collected at −20, −10 min, 0 pre-glucose infusions (baseline), and at 10, 20, 30, 40, 50, and 60 minutes.

A representation of the data are shown in table 9.

TABLE 9

| | 5 mg/Kg/min | 15 mg/Kg/min |
|---|---|---|
| Vehicle | 4.3 ± 0.2 (n = 18) | 12.7 ± 0.9 (n = 18) |
| 0.0179 mg/Kg | 5.6 ± 0.4 (n = 4) | 15.9 ± 1.8 (n = 4) |
| 0.179 mg/Kg | 9.0 ± 1.1* (n = 6) | 28.0 ± 3.8* (n = 6) |
| 1.79 mg/Kg | 20.5 ± 3.0* (n = 4) | 52.7 ± 7.2* (n = 4) |

*P ≦ 0.05 versus vehicle

---

We claim:

1. A method of treating a patient with non-insulin dependent diabetes mellitus comprising administering to the patient a therapeutically effective amount of a heterologous fusion protein comprising:

a GLP-1 analog comprising SEQ ID NO: 1

His-Xaa$_8$-Glu-Gly-Thr-Phe-Thr-Ser-Asp-Val-Ser-Ser-

Tyr-Leu-Glu-Glu-Gln-Ala-Ala-Lys-Glu-Phe-Ile-Ala-

Trp-Leu-Val-Lys-Gly-Gly-Gly wherein Xaa$_8$ is Gly;

an Fc portion of an immunoglobulin comprising SEQ ID NO: 7

Ala-Glu-Ser-Lys-Tyr-Gly-Pro-Pro-Cys-Pro-Pro-Cys-

Pro-Ala-Pro-Xaa$_{16}$-Xaa$_{17}$-Xaa$_{18}$-Gly-Gly-Pro-Ser-Val-

Phe-Leu-Phe-Pro-Pro-Lys-Pro-Lys-Asp-Thr-Leu-Met-

Ile-Ser-Arg-Thr-Pro-Glu-Val-Thr-Cys-Val-Val-Val-

Asp-Val-Ser-Gln-Glu-Asp-Pro-Glu-Val-Gln-Phe-Asn-

Trp-Tyr-Val-Asp-Gly-Val-Glu-Val-His-Asn-Ala-Lys-

Thr-Lys-Pro-Arg-Glu-Glu-Gln-Phe-Xaa$_{80}$-Ser-Thr-Tyr-

Arg-Val-Val-Ser-Val-Leu-Thr-Val-Leu-His-Gln-Asp-

Trp-Leu-Asn-Gly-Lys-Glu-Tyr-Lys-Cys-Lys-Val-Ser-

Asn-Lys-Gly-Leu-Pro-Ser-Ser-Ile-Glu-Lys-Thr-Ile-

Ser-Lys-Ala-Lys-Gly-Gln-Pro-Arg-Glu-Pro-Gln-Val-

Tyr-Thr-Leu-Pro-Pro-Ser-Gln-Glu-Glu-Met-Thr-Lys-

Asn-Gln-Val-Ser-Leu-Thr-Cys-Leu-Val-Lys-Gly-Phe-

Tyr-Pro-Ser-Asp-Ile-Ala-Val-Glu-Trp-Glu-Ser-Asn-

Gly-Gln-Pro-Glu-Asn-Asn-Tyr-Lys-Thr-Thr-Pro-Pro-

Val-Leu-Asp-Ser-Asp-Gly-Ser-Phe-Phe-Leu-Tyr-Ser-

Arg-Leu-Thr-Val-Asp-Lys-Ser-Arg-Trp-Gln-Glu-Gly-

Asn-Val-Phe-Ser-Cys-Ser-Val-Met-His-Glu-Ala-Leu-

His-Asn-His-Tyr-Thr-Gln-Lys-Ser-Leu-Ser-Leu-Ser-

Leu-Gly-Xaa$_{230}$ wherein:
Xaa at position 16 is Glu;
Xaa at position 17 is Ala;
Xaa at position 18 is Ala;
Xaa at position 80 is Asn; and
Xaa at position 230 is Lys or absent;
and a peptide linker comprising SEQ ID NO: 8

Gly-Gly-Gly-Gly-Ser-Gly-Gly-Gly-Gly-Ser-Gly-Gly-

Gly-Gly-Ser wherein the N-terminal glycine of the peptide linker is directly fused to the C-terminal glycine residue of the GLP-1 analog and the C-terminal serine of the peptide linker is directly fused to N-terminal alanine of the Fc portion.

2. A method of treating a patient with non-insulin dependent diabetes mellitus comprising administering to the patient a therapeutically effective amount of a heterologous fusion protein consisting of:

a GLP-1 analog consisting of SEQ ID NO:1

His-Xaa$_8$-Glu-Gly-Thr-Phe-Thr-Ser-Asp-Val-Ser-Ser-

Tyr-Leu-Glu-Glu-Gln-Ala-Ala-Lys-Glu-Phe-Ile-Ala-

Trp-Leu-Val-Lys-Gly-Gly-Gly wherein Xaa$_8$ is Gly;

an Fc portion of an immunoglobulin consisting of SEQ ID NO:7

Ala-Glu-Ser-Lys-Tyr-Gly-Pro-Pro-Cys-Pro-Pro-Cys-

Pro-Ala-Pro-Xaa$_{16}$-Xaa$_{17}$-Xaa$_{18}$-Gly-Gly-Pro-Ser-Val-

Phe-Leu-Phe-Pro-Pro-Lys-Pro-Lys-Asp-Thr-Leu-Met-

Ile-Ser-Arg-Thr-Pro-Glu-Val-Thr-Cys-Val-Val-Val-

Asp-Val-Ser-Gln-Glu-Asp-Pro-Glu-Val-Gln-Phe-Asn-

Trp-Tyr-Val-Asp-Gly-Val-Glu-Val-His-Asn-Ala-Lys-

Thr-Lys-Pro-Arg-Glu-Glu-Gln-Phe-Xaa$_{80}$-Ser-Thr-Tyr-

Arg-Val-Val-Ser-Val-Leu-Thr-Val-Leu-His-Gln-Asp-

Trp-Leu-Asn-Gly-Lys-Glu-Tyr-Lys-Cys-Lys-Val-Ser-

Asn-Lys-Gly-Leu-Pro-Ser-Ser-Ile-Glu-Lys-Thr-Ile-

Ser-Lys-Ala-Lys-Gly-Gln-Pro-Arg-Glu-Pro-Gln-Val-

Tyr-Thr-Leu-Pro-Pro-Ser-Gln-Glu-Glu-Met-Thr-Lys-

Asn-Gln-Val-Ser-Leu-Thr-Cys-Leu-Val-Lys-Gly-Phe-

Tyr-Pro-Ser-Asp-Ile-Ala-Val-Glu-Trp-Glu-Ser-Asn-

Gly-Gln-Pro-Glu-Asn-Asn-Tyr-Lys-Thr-Thr-Pro-Pro-

Val-Leu-Asp-Ser-Asp-Gly-Ser-Phe-Phe-Leu-Tyr-Ser-

Arg-Leu-Thr-Val-Asp-Lys-Ser-Arg-Trp-Gln-Glu-Gly-

Asn-Val-Phe-Ser-Cys-Ser-Val-Met-His-Glu-Ala-Leu-

His-Asn-His-Tyr-Thr-Gln-Lys-Ser-Leu-Ser-Leu-Ser-

Leu-Gly-Xaa$_{230}$ wherein:
Xaa at position 16 is Glu;
Xaa at position 17 is Ala;
Xaa at position 18 is Ala;

Xaa at position 80 is Asn; and
Xaa at position 230 is Lys or absent;
and a peptide linker consisting of SEQ ID NO:8

Gly-Gly-Gly-Gly-Ser-Gly-Gly-Gly-Gly-Ser-Gly-Gly-
Gly-Gly-Ser wherein the N-terminal glycine of the peptide linker is directly fused to the C-terminal glycine residue of the GLP-1 analog and the C-terminal serine of the peptide linker is directly fused to N-terminal alanine of the Fc portion.

3. A method of treating a patient with non-insulin dependent diabetes mellitus comprising administering to the patient a therapeutically effective amount of a heterologous fusion protein comprising a dimer comprising two chains joined together by disulfide bonds wherein each chain has:
a GLP-1 analog consisting of SEQ ID NO: 1

His-Xaa$_8$-Glu-Gly-Thr-Phe-Thr-Ser-Asp-Val-Ser-Ser-
Tyr-Leu-Glu-Glu-Gln-Ala-Ala-Lys-Glu-Phe-Ile-Ala-
Trp-Leu-Val-Lys-Gly-Gly-Gly, wherein Xaa$_8$ is Gly;
an Fc portion of an immunoglobulin comprising SEQ ID NO:7

Ala-Glu-Ser-Lys-Tyr-Gly-Pro-Pro-Cys-Pro-Pro-Cys-
Pro-Ala-Pro-Xaa$_{16}$-Xaa$_{17}$-Xaa$_{18}$-Gly-Gly-Pro-Ser-Val-
Phe-Leu-Phe-Pro-Pro-Lys-Pro-Lys-Asp-Thr-Leu-Met-
Ile-Ser-Arg-Thr-Pro-Glu-Val-Thr-Cys-Val-Val-Val-
Asp-Val-Ser-Gln-Glu-Asp-Pro-Glu-Val-Gln-Phe-Asn-
Trp-Tyr-Val-Asp-Gly-Val-Glu-Val-His-Asn-Ala-Lys-
Thr-Lys-Pro-Arg-Glu-Glu-Gln-Phe-Xaa$_{80}$-Ser-Thr-Tyr-
Arg-Val-Val-Ser-Val-Leu-Thr-Val-Leu-His-Gln-Asp-
Trp-Leu-Asn-Gly-Lys-Glu-Tyr-Lys-Cys-Lys-Val-Ser-
Asn-Lys-Gly-Leu-Pro-Ser-Ser-Ile-Glu-Lys-Thr-Ile-
Ser-Lys-Ala-Lys-Gly-Gln-Pro-Arg-Glu-Pro-Gln-Val-
Tyr-Thr-Leu-Pro-Pro-Ser-Gln-Glu-Glu-Met-Thr-Lys-
Asn-Gln-Val-Ser-Leu-Thr-Cys-Leu-Val-Lys-Gly-Phe-
Tyr-Pro-Ser-Asp-Ile-Ala-Val-Glu-Trp-Glu-Ser-Asn-
Gly-Gln-Pro-Glu-Asn-Asn-Tyr-Lys-Thr-Thr-Pro-Pro-
Val-Leu-Asp-Ser-Asp-Gly-Ser-Phe-Phe-Leu-Tyr-Ser-
Arg-Leu-Thr-Val-Asp-Lys-Ser-Arg-Trp-Gln-Glu-Gly-
Asn-Val-Phe-Ser-Cys-Ser-Val-Met-His-Glu-Ala-Leu-
His-Asn-His-Tyr-Thr-Gln-Lys-Ser-Leu-Ser-Leu-Ser-
Leu-Gly-Xaa$_{230}$, wherein Xaa at position 16 is Glu;
Xaa at position 17 is Ala;
Xaa at position 18 is Ala;
Xaa at position 80 is Asn; and Xaa at position 230 is absent; and
a peptide linker consisting of SEQ ID NO: 8

Gly-Gly-Gly-Gly-Ser-Gly-Gly-Gly-Gly-Ser-Gly-Gly-
Gly-Gly-Ser wherein the N-terminal glycine of the peptide linker is directly fused to the C-terminal glycine residue of the GLP-1 analog and the C-terminal serine of the peptide linker is directly fused to N-terminal alanine of the Fc portion.

4. A method of treating a patient with non-insulin dependent diabetes mellitus comprising administering to the patient a therapeutically effective amount of a heterologous fusion protein comprising a dimer comprising two chains joined together by disulfide bonds wherein each chain has:
a GLP-1 analog consisting of SEQ ID NO:1

His-Xaa$_8$-Glu-Gly-Thr-Phe-Thr-Ser-Asp-Val-Ser-Ser-
Tyr-Leu-Glu-Glu-Gln-Ala-Ala-Lys-Glu-Phe-Ile-Ala-
Trp-Leu-Val-Lys-Gly-Gly-Gly, wherein Xaa$_8$ is Gly;

Ala-Glu-Ser-Lys-Tyr-Gly-Pro-Pro-Cys-Pro-Pro-Cys-
Pro-Ala-Pro-Xaa$_{16}$-Xaa$_{17}$-Xaa$_{18}$-Gly-Gly-Pro-Ser-Val-
Phe-Leu-Phe-Pro-Pro-Lys-Pro-Lys-Asp-Thr-Leu-Met-
Ile-Ser-Arg-Thr-Pro-Glu-Val-Thr-Cys-Val-Val-Val-
Asp-Val-Ser-Gln-Glu-Asp-Pro-Glu-Val-Gln-Phe-Asn-
Trp-Tyr-Val-Asp-Gly-Val-Glu-Val-His-Asn-Ala-Lys-
Thr-Lys-Pro-Arg-Glu-Glu-Gln-Phe-Xaa$_{80}$-Ser-Thr-Tyr-
Arg-Val-Val-Ser-Val-Leu-Thr-Val-Leu-His-Gln-Asp-
Trp-Leu-Asn-Gly-Lys-Glu-Tyr-Lys-Cys-Lys-Val-Ser-
Asn-Lys-Gly-Leu-Pro-Ser-Ser-Ile-Glu-Lys-Thr-Ile-
Ser-Lys-Ala-Lys-Gly-Gln-Pro-Arg-Glu-Pro-Gln-Val-
Tyr-Thr-Leu-Pro-Pro-Ser-Gln-Glu-Glu-Met-Thr-Lys-
Asn-Gln-Val-Ser-Leu-Thr-Cys-Leu-Val-Lys-Gly-Phe-
Tyr-Pro-Ser-Asp-Ile-Ala-Val-Glu-Trp-Glu-Ser-Asn-
Gly-Gln-Pro-Glu-Asn-Asn-Tyr-Lys-Thr-Thr-Pro-Pro-
Val-Leu-Asp-Ser-Asp-Gly-Ser-Phe-Phe-Leu-Tyr-Ser-
Arg-Leu-Thr-Val-Asp-Lys-Ser-Arg-Trp-Gln-Glu-Gly-
Asn-Val-Phe-Ser-Cys-Ser-Val-Met-His-Glu-Ala-Leu-
His-Asn-His-Tyr-Thr-Gln-Lys-Ser-Leu-Ser-Leu-Ser-
Leu-Gly-Xaa$_{230}$, wherein Xaa at position 16 is Glu;
Xaa at position 17 is Ala;
Xaa at position 18 is Ala;
Xaa at position 80 is Asn; and
Xaa at position 230 is Lys; and
a peptide linker consisting of SEQ ID NO:8

Gly-Gly-Gly-Gly-Ser-Gly-Gly-Gly-Gly-Ser-Gly-Gly-Gly-Gly-Ser wherein the N-terminal glycine of the peptide linker is directly fused to the C-terminal glycine residue of the GLP-1 analog and the C-terminal serine of the peptide linker is directly fused to N-terminal alanine of the Fc portion.

5. The method according to any one of claims 1 to 4 wherein the fusion protein is produced by expressing the fusion protein in a mammalian host cell.

6. The method according to claim 5 wherein the host cell is a CHO cell.

* * * * *

UNITED STATES PATENT AND TRADEMARK OFFICE
CERTIFICATE OF CORRECTION

PATENT NO. : 8,273,854 B2
APPLICATION NO. : 12/262832
DATED : September 25, 2012
INVENTOR(S) : Wolfgang Glaesner et al.

It is certified that error appears in the above-identified patent and that said Letters Patent is hereby corrected as shown below:

Claim 4, column 36, lines 28-29:

after "Gly;" insert --an Fc portion of an immunoglobulin comprising SEQ ID NO:7--

Signed and Sealed this
Twenty-seventh Day of November, 2012

David J. Kappos
*Director of the United States Patent and Trademark Office*